United States Patent [19]

Yang et al.

[11] Patent Number: 5,681,301
[45] Date of Patent: Oct. 28, 1997

[54] BACKING WEB IN AN ABSORBENT ARTICLE

[75] Inventors: Ching-Yun Morris Yang; Mordechai Turi, both of Princeton Junction; William Chien-Chung Hsu, Edison, all of N.J.

[73] Assignee: Johnson & Johnson Worldwide Absorbent Products, New Brunswick, N.J.

[21] Appl. No.: 590,099

[22] Filed: Jan. 24, 1996

[51] Int. Cl.$^6$ ............................ A61F 13/15; A61F 13/20
[52] U.S. Cl. .................. 604/370; 604/373; 604/385.2; 602/41; 602/58; 602/59; 428/137; 428/315.5
[58] Field of Search .............................. 604/358, 370, 604/372, 373, 385.1, 385.2, 393, 400; 601/41–47, 52, 58; 428/137, 315.5, 913

[56] References Cited

U.S. PATENT DOCUMENTS

| | | | |
|---|---|---|---|
| 3,881,489 | 5/1975 | Hartwell | 604/370 |
| 4,045,833 | 9/1977 | Mesek et al. | 604/370 |
| 4,147,580 | 4/1979 | Buell | 604/370 |
| 4,272,473 | 6/1981 | Riemersma et al. | |
| 4,341,216 | 7/1982 | Obenour | 604/370 |
| 4,388,075 | 6/1983 | Mesek et al. | |
| 4,591,523 | 5/1986 | Thompson | |
| 4,609,518 | 9/1986 | Curro et al. | |
| 4,772,444 | 9/1988 | Curro et al. | |
| 4,778,664 | 10/1988 | Curro et al. | |
| 4,822,350 | 4/1989 | Ito et al. | 604/370 |
| 5,098,764 | 3/1992 | Drelich et al. | |
| 5,158,819 | 10/1992 | Goodman et al. | |
| 5,221,276 | 6/1993 | Battrell | |
| 5,244,711 | 9/1993 | Drelich et al. | |
| 5,269,981 | 12/1993 | Jameson et al. | |
| 5,322,728 | 6/1994 | Davey et al. | |
| 5,498,581 | 3/1996 | Welch et al. | |
| 5,498,582 | 3/1996 | Krause et al. | |

FOREIGN PATENT DOCUMENTS

| | | | |
|---|---|---|---|
| 0192965 | 9/1986 | European Pat. Off. | 604/358 |
| 0274753 | 7/1988 | European Pat. Off. | 604/358 |
| 3306843 | 9/1983 | Germany | 604/358 |
| 2282003 | 12/1987 | Japan | 604/358 |
| 93/15701 | 8/1993 | WIPO | |
| 94/04112 | 3/1994 | WIPO | |

*Primary Examiner*—P. Zuttarelli
*Attorney, Agent, or Firm*—Dressler, Rockey, Milnamow & Katz, Ltd.

[57] ABSTRACT

A disposable absorbent article comprises an absorbent panel and a backing web secured to the panel. A preferred form of the web comprises an apertured film. The web may also include other components on the apertured film, including adhesive. The apertured film is preferably produced from a solid precursor film. The precursor film comprises a copolymer of ethylene and a comonomer polymerized using a single-site metallocene-type polymerization catalyst. The apertured film is formed from the precursor film so that the apertured film has localized deformations and apertures therein. The apertured film exhibits breathability, strength, and flexibility with an elasticity accommodating stretch or elongation and at least partial recovery.

20 Claims, 18 Drawing Sheets

BACKING WEB IN AN ABSORBENT ARTICLE

TECHNICAL FIELD

The present invention relates to a backing web or film for use in an absorbent article. The invention is particularly suitable for incorporation in an adhesive bandage.

BACKGROUND OF THE INVENTION AND TECHNICAL PROBLEMS POSED BY THE PRIOR ART

Absorbent panels or members are typically supported or carried by a backing sheet, web, film, or the like, and the assembly is typically adapted to be held against, or secured to, a person's skin. Well known absorptive devices include disposable diapers, feminine sanitary protection articles, incontinent articles, bandages, and the like.

Typically, such absorbent articles can be held in contact with the body by a variety of means, including belts, closures which fasten one part of the article to another part of the article tightly around the wearer (e.g., such as diaper adhesive closures or safety pins), and adhesive portions of the article adhering directly to the wearer's skin.

Although a variety of absorbent article designs have been proposed and/or are in use, there is a need to provide improved absorbent articles with enhanced properties or characteristics that users find desirable. In particular, in many applications, it would be desirable to provide an improved backing web that exhibits an increased elasticity. For example, the skin on many portions of the human body stretches up to 30%. In areas such as knuckles, knees, and elbows, the skin may stretch up to 50%. Therefore, it would be desirable to provide an absorbent article which can accommodate such stretching.

It would be especially desirable to provide an improved backing web for a bandage which could accommodate the relatively great stretching of skin that occurs at the knuckles, knees, and elbows. Such an improved backing web could reduce the amount of stress in the adhesive and would thereby minimize the movement between the absorbent article and the skin. It would also be more comfortable to wear owing to a substantial reduction in mechanical irritation and transfer of attachment adhesive to the skin.

Further, it would be desirable to provide an improved absorbent article in which the backing web is very flexible and can be stretched with a relatively low force. The backing web should preferably exhibit low energy loss and a high immediate recovery. The backing web should also preferably have good toughness—preferably comparable to, or better than, conventional polyethylene films.

Further, such an improved absorbent article should preferably exhibit good breathability (i.e., permeability to air and water vapor). A backing web that does not breath, or that does not breath sufficiently, can cause maceration, especially in overlapped areas, where the skin softens and wears away.

Increased breathability would also accommodate greater heat transfer between the skin and the ambient air. Additionally, the improved absorbent article backing web should preferably have a high moisture or water vapor transfer rate even after an adhesive coating has been applied. This can reduce warm or sweaty sensations with respect to the skin under the article.

Although increased breathability of an absorbent article is desirable, it would also be beneficial to provide an improved backing web which is water-resistant and non-absorbing, and which is substantially impermeable to liquids such as water. A substantially liquid-impervious web is particularly desirable for use as a backing sheet in single-use absorbent structures, such as diapers and the like.

It would also be advantageous to provide an improved absorbent article in which the backing sheet has sufficient strength to withstand normal wear. Preferably, when incorporated in an exposed bandage, the backing web should have sufficient strength to provide resistance to tearing or abrasion. Further, the absorbent article should be sufficiently strong to maintain its integrity for a sufficiently long period of time while it is being worn and subjected to compressive forces, external impact forces, flexural forces, fluids from the wearer's body, or external liquids.

Preferably, such an improved absorbent article should be comfortable to wear. The article should desirably feel good to the wearer and should preferably have soft, cloth-like drape and feel characteristics.

Further, it would be advantageous to provide such an improved absorbent article with a backing web having the capability for receiving an adhesive coating without deleteriously affecting the other desirable characteristics of the web to a significant degree.

Additionally, it would be desirable if the backing web for such an improved absorbent article could also accommodate a variety of surface patterns and could be provided in a variety of colors. Further, it would be advantageous if the absorbent article backing web could accept decorative printing.

Additionally, the backing web should preferably be radiation sterilizable.

Finally, it would be desirable to provide an absorbent article with an improved backing web design and material composition that accommodates manufacturing processability and minimizes manufacturing costs.

The present invention provides an improved backing web in an absorbent article which can accommodate designs having the above-discussed benefits and features.

SUMMARY OF THE INVENTION

The inventors have recognized that conventional designs for absorbent articles do not provide the above-discussed beneficial features and characteristics to the extent that is desired by wearers of such articles. The present invention provides heretofore unrecognized combinations of all or many of the above-discussed features in a single absorbent article design. Further, the invention provides such an absorbent article design with improved characteristics to an extent not previously thought possible.

In particular, according to one aspect of the invention, a disposable absorbent article comprises an absorbent panel and a backing web of the invention secured to the absorbent panel. The web comprises a polymeric film having apertures. The film exhibits an elasticity accommodating at least a 50% stretch elongation when subjected to a tension force of at least 0.5 pounds per inch of film width (i.e., the width dimension of a specimen of the film which is transverse to the tension force direction) and exhibiting a recovery of at least 65% from a stretch elongation of 50%.

According to another aspect of the invention, a backing web that is secured to an absorbent panel comprises an apertured film produced from a solid precursor film. The precursor film comprises a copolymer of ethylene and a comonomer polymerized in a polymer structure using a single-site metallocene, or metallocene-type, polymerization catalyst. Preferably, the metallocene-polymerized copolymer has a density in the range of about 0.86 to about 0.95 g/cm³, a molecular weight distribution in the range of about 1.0 to about 3.5, and a melt index in the range of about 0.5 to about 10.0 g/10 min. The apertured film is produced from the precursor film by subjecting the precursor film to forming forces sufficient to form permanent, localized deformations therein and create apertures therein.

According to yet another aspect of the invention, a disposable absorbent article is provided with a backing web secured to an absorbent panel wherein the backing web comprises an apertured polymeric film. The polymeric film also exhibits an elasticity such that the tension force within the range of about 0.5 to about 2.5 pounds per inch of film width (i.e., the width dimension of a specimen of the film which is transverse to the tension force direction) will produce a 50% stretch elongation with a recovery of at least 65%.

According to another aspect of the invention, an absorbent panel is secured to a backing web. The backing web includes at least an apertured film produced from a solid precursor film comprising a copolymer of ethylene and a comonomer polymerized (preferably in a block and branched polymer structure) using a single-site metallocene-type polymerization catalyst. The apertured film has localized deformations and apertures therein. The film exhibits breathability, strength, and flexibility with an elasticity accommodating stretch elongation and at least partial recovery.

The invention, according to another aspect, provides a web suitable for contact with skin. The web comprises a polymeric film having apertures providing breathability with resistance to water permeation and to water absorption. The film is flexible and has an elasticity accommodating a stretch elongation of at least 50% with a recovery of at least 65%.

The invention thus allows the fabrication of an improved absorbent article having a fabric-like feel and exhibiting, among other things, increased strength, elasticity, water vapor permeability, and water resistance.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

Figure 1:
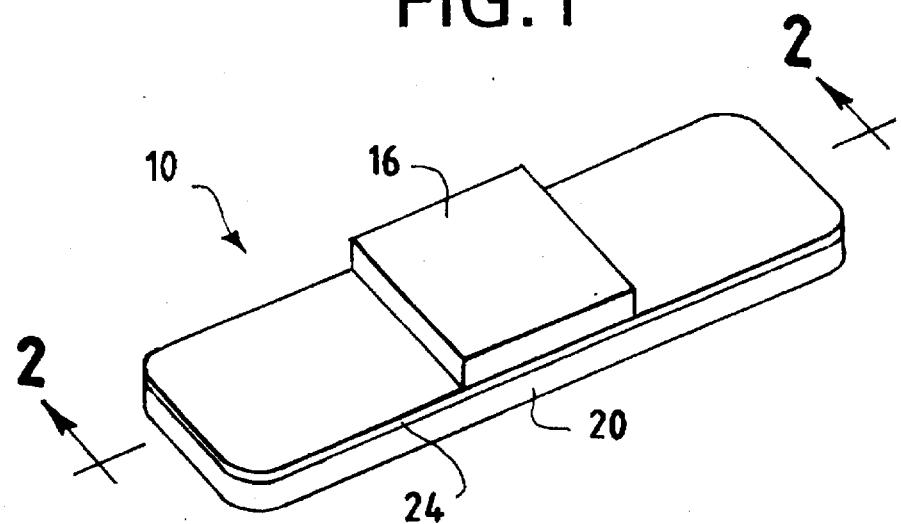
FIG. 1 is a simplified, perspective representation of an absorbent article in the form of a bandage, the components' thicknesses having been greatly exaggerated for ease of illustration.

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the absorbent articles embodying this invention are described in a position in which the absorbent panel is on top of the backing web and faces upwardly. Terms such as upper, lower, horizontal, etc., are used with reference to this position. It will be understood, however, that the articles embodying this invention may be manufactured, stored, transported, used, and sold in an orientation other than the position described.

The absorbent articles may incorporate certain conventional components or structures the details of which, although not fully illustrated or described, will be apparent to those having skill in the art and an understanding of the necessary functions of such components.

As used herein, the abbreviation "MVTR" stands for "Moisture Vapor Transmission Rate" that may alternatively be designated "Water Vapor Transmission Rate" ("WVTR") which is defined, and for which values are determined, as set forth in the American Society Of Testing And Materials standard ASTM F 1249-90.

As used herein, the abbreviation "ECD" stands for the "equivalent circular diameter" (i.e., diameter of a circle) having the same area as an irregularly shaped hole and is calculated in accordance with the following formula: ECD= $(4A/\pi)^{1/2}$, where A is equal to the area of the irregularly shaped hole.

As used herein, the term "ECD COV (%)" stands for the coefficient of variation determined by the formula: ECD COV=100 (SD/mean value of the ECD values), where SD is the standard deviation of the ECD values.

As used herein, the term "molecular weight distribution" (MWD) has a definition as set forth in the U.S. Pat. No. 5,322,728 at column 4, lines 50–57.

As used herein, the term "polymer" or "polymeric" refers to a macromolecule formed by the chemical union of multiple identical or different combining units called monomers.

As used herein, the abbreviation "MD" stands for the "machine direction" and refers to the direction of movement of a web of film material through a machine which produces or further processes the web.

As used herein, the abbreviation "CD" stands for the "cross direction" and refers to the direction across the width of a web perpendicular to the machine direction (MD).

The term "Frazier Air Permeability" as used herein refers to the air flow rate in cubic feet per minute per square foot through a web or film specimen as determined in accordance with the American Society Of Testing And Materials standard ASTM D 737-75 (Reapproved 1980).

As used herein, the "melt index" is the measurement (in units of g/10 min.) of the amount of a polymer passed through a molder or extruder under specified conditions, as defined in the American Society Of Testing And Materials standard ASTM D-1238.

As used herein in conjunction with a tension force applied to a film (or web) of a given thickness, the term "pounds per inch of film (or web)" refers to the application of the tension force across a one-inch dimension of the film (or web) as measured in a direction perpendicular to the direction in which the tension force is applied (i.e., perpendicular to the line of action of the tension force).

As used herein, the term "recovery" is the immediate recovery or percent retraction of a web or film sample specimen from a stretched condition or elongation. It is measured according to a test procedure described in detail hereinafter, and it can be calculated in accordance with the following formula:

$$\text{immediate recovery} = \frac{(Le - Lt)}{(Le - Lt)} \times 100$$

where

Lo is an original specimen gauge length (selected to be 4.0 inches in the procedure described below);

Le is the extended or stretched specimen length (selected to be 6.0 inches in the procedure described below); and Lt is the post-tension length of the specimen immediately upon release of the stretching force.

In the above-listed formula, the term (Le-Lt) may be defined as the "recovery distance" of the previously stretched specimen.

The specimen is tested according to the following described procedure wherein a standard 4.0 inch gauge length portion of the specimen is first stretched to a specified standard elongation of 50% (i.e., to 6.0 inches) at a controlled rate of speed a is subsequently immediately permitted to relax (contract) at the same controlled rate of speed until the tension force becomes zero.

In particular, the tension force is applied to the specimen by a machine (e.g., an INSTRON brand testing machine) wherein the specimen is held between two clamps and strained by a uniform movement of the pulling clamp. Each clamp has one jaw gripping surface which is an integral part of the rigid frame of the clamp, while the other gripping surface is on a part that is hinged or swiveled to the movable member of the clamp. The gripping surfaces on each jaw measure 1 inch by at least 1½ inches, with the long dimension being perpendicular to the direction of application of the load. The jaws have smooth gripping surfaces which are sufficiently flat and parallel to prevent slippage of the specimen during the test. All edges which might cause a cutting action are rounded to a radius of not over 1/64 inch. The gripping surfaces may be rubber-faced to help prevent slippage.

The specimen or sample is cut with the sides parallel. The specimen length is not less than 6 inches and the width is 1.0 inch. The specimen is conditioned for at least 4 hours at a relative humidity of 50%±2% at 73° F.±2° F.0

The specimen is clamped firmly and squarely in the jaws of the clamps so that the distance between the clamps at the start of the test is 4.0 inches to establish the standard specimen 4.0 inch gauge length (Lo) between the clamps. The machine cycle extension limits are set to reflect the amount of extension or stretch to which the specimen is to be subjected (i.e., a standard 2.0 inches beyond the standard 4.0 inch gauge length in this test procedure).

Force is applied to the specimen with the pulling clamp programmed to move at a rate of 5 inches/minute±0.1 inch per minute until the portion of the specimen between the clamps is stretched to the specified standard 6.0 inch extended length Le. The stretched specimen is then immediately allowed to contract (relax) at a uniform rate of 5 inches per minute±0.1 inch per minute. The tension force on the specimen is constantly measured, and the defined post-tension length (Lt) of the fully relaxed (contracted) specimen is reached immediately upon the tension force dropping to zero. The recovery distance (Le–Lt) is then computed for use in determining the immediate recovery of the specimen pursuant to the above described formula.

As used herein, the term "stretch energy" is the energy required to stretch a specimen from an original length Lo to an extended length Le (where Lo and Le are defined above in the discussion of the term "recovery"). The stretch energy equals the area under the stress-strain curve from the original length Lo to the extended length Le.

As used herein, the term "recovery energy" is the energy released by a specimen in returning from an extended length Le to a post-tension, relaxed length Lt (where Le and Lt are defined above in the discussion of the term "recovery"). The recovery energy equals the area under the stress-strain curve from the extended length Le to the relaxed length Lt.

As used herein, the term "tensile strength" is the force required to break or rupture a specimen of a web per lineal inch of the web transverse to the tension force. The value thereof is determined for a one inch wide specimen as set forth according to the following 10 test procedure wherein a continually increasing load is applied longitudinally to the specimen until rupture. Values for the breaking load are recorded.

Specifically, the test sample specimen is a rectangular strip with parallel sides. The length is not less than 5.5 inches, and the width is 1.0 inches. The sample specimen is conditioned for at least 4 hours at a relative humidity of 50%±2% at 73 ° F.±2° F. A tensile force is applied by a testing machine wherein the specimen is held between two clamps and strained by a uniform movement of the pulling clamp. The clamps have the same design as described above for the machine used to determine the "immediate recovery".

The test specimen is clamped firmly and squarely in the jaws of the clamps with the distance between clamps at the start of the test being 3 inches. Force is applied to the specimen at such a rate that the pulling clamp will travel at a uniform speed of 12.0±0.5 inches per min.—provided that the time of breaking shall be 10 seconds±5 seconds. If the breaking time is more or less, the speed of pull is adjusted to a slower speed to insure a breaking time of 10 seconds±5 seconds. The average breaking force of at least 5 specimens for each direction tested (MD or CD) is reported as the "tensile strength".

Figure 2:
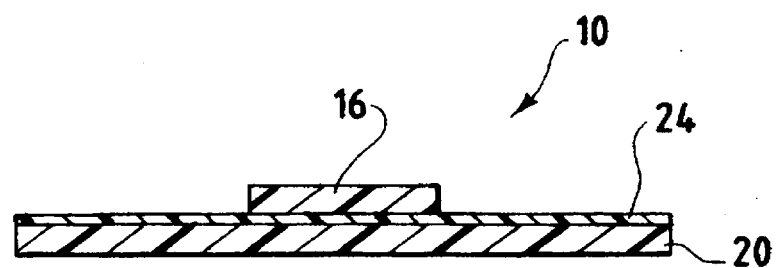
FIG. 2 is an enlarged, fragmentary cross section taken generally along the plane 2—2 in FIG. 1.
Figure 3:
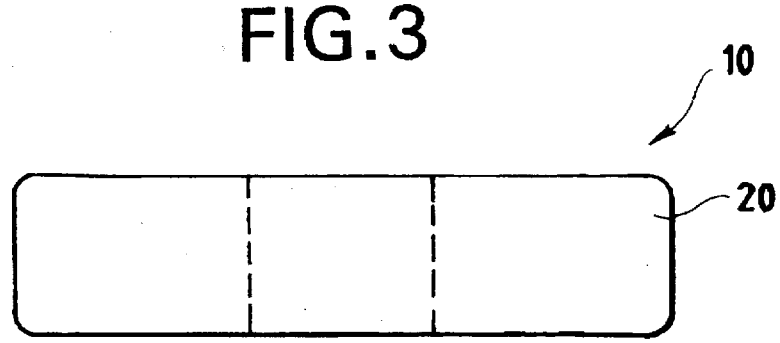
FIG. 3 is a bottom plan view of the absorbent article of FIG. 1.

FIGS. 1, 2, and 3 show an embodiment of the invention as incorporated in a disposable absorbent article in the form of a bandage 10 having an absorbent panel or pad 16 secured to a backing web or film 20. The upwardly facing surface of the backing web 20 is coated with an adhesive 24 for securing the bandage to skin. The panel 16 may be secured to the web 20 with the same, or a different, adhesive.

Although not illustrated, the bandage 10 may be provided with conventional adhesive release tapes or tabs covering the exposed adhesive 24 and loosely overlying the absorbent panel 16. In addition, although not illustrated, a conventional wound release cover may also be secured to the top of the absorbent panel 16.

Although not illustrated, the bandage 10 may have an "island" type dressing (i.e., absorbent panel or pad) wherein the width of the dressing, as well as the length of the dressing, are less than the width and length, respectively, of the film. The film would have a layer of adhesive extending over the entire surface of the film facing the dressing. The film could thus be secured to skin all around the periphery of the dressing.

FIGS. 1, 2, and 3 represent the bandage 10 in a simplified manner and do not show the detailed structure of the absorbent pad and backing web. The absorbent panel 16 may have any suitable conventional or special structure known to those having skill in the art. The detailed structure of the backing web 20 is described in detail hereinafter.

According to one aspect of the invention, the preferred form of the backing web or film 20 includes deflated balloon-like bubbles and tubes. The tubes have oval or irregular shapes and have open ends. These structures do not all begin and terminate at the same heights in the film. These bubbles and tube structures are generally irregular and have no uniform base and/or termination portion. The structures are formed as local deformations by forcing or stretching a solid precursor web or film into unsupported areas of a three-dimensional forming member as described hereinafter in detail. The deflated bubbles and the tubes with holes are formed as a result of deforming the web or film into unbursted and bursted local deformations, respectively. These structures give the web 20 a soft, fabric feel.

Various levels of deformation can be formed in the web or film, including undulatory ribs, ridges, or wales. This may emulate the crosswise undulatory ribs of tricot-type fabric. In one preferred form of the web, the ratio of burst area formations (e.g., tubes) to unbursted areas (e.g., bubbles) ranges from about 90/10 to about 20/80, with the preferred ratio being in a range of about 70/30 to about 30/70. The deformed, thin membrane-type portions of the film with minimal contact surface provide a very soft feel.

The apertured film may be produced by a preferred process described in detail hereinafter wherein deformations and apertures are formed in the film by columnar water jets while the film is supported on a three-dimensional forming surface. The preferred form of the apertured web or film may be characterized as including (1) a first side which has been impacted by the water jets and which defines a three-dimensional surface structure, and (2) an oppositely facing second side which was forced against the forming surface and which also has a three-dimensional surface structure. Preferably, the first side has first, second, third, and fourth surfaces. The first surface defines a plurality of undulating ridges or wales generally arranged in rows. The second surface slopes to connect the first surface and third surface. The third surface has sloping entrance cavities or macroscopic apertures which connect to a fourth surface containing a hole and/or bubble, or containing a cluster of holes and/or bubbles. 5 The macroscopic apertures or cavities, in the presently preferred embodiments, are arranged generally in rows in the third surface.

The terms "cavities" and "apertures" are used interchangeably and describe the void regions defined in the third surface. In the preferred embodiment, not all of the cavities or apertures in the third surface are completely closed by the fourth surface which defines the through holes establishing communication between some of the third surface cavities or apertures and the other side (i.e., second side) of the film. In other embodiments, most or all of the cavities or apertures in the third surface may terminate in, or be closed by, a solid fourth surface which would have no (or only a few) through holes to the other side of the film (i.e., second side of the film). Such web embodiments having few or no through holes may be more suitable for use as a backing web in a sanitary protection article or disposable diaper (described hereinafter in more detail).

The film second side exhibits generally a negative image of the first side and includes tubes with closed distal ends and/or includes deflated balloon-like bubbles. Such tubes and bubbles may also be generally grouped in clusters. In the preferred embodiment, the tubes have oval or irregular shapes. In the preferred embodiment, there are a substantial number of tubes terminating in holes. The tube and bubble structures impart a soft, fabric-like feel to that side of the apertured web or film.

The apertured web or film can be produced from a starting film, or precursor film, which is not apertured and which can accommodate significant elastic stretching. Preferred compositions of such a precursor film are described in detail hereinafter.

Figure 14:
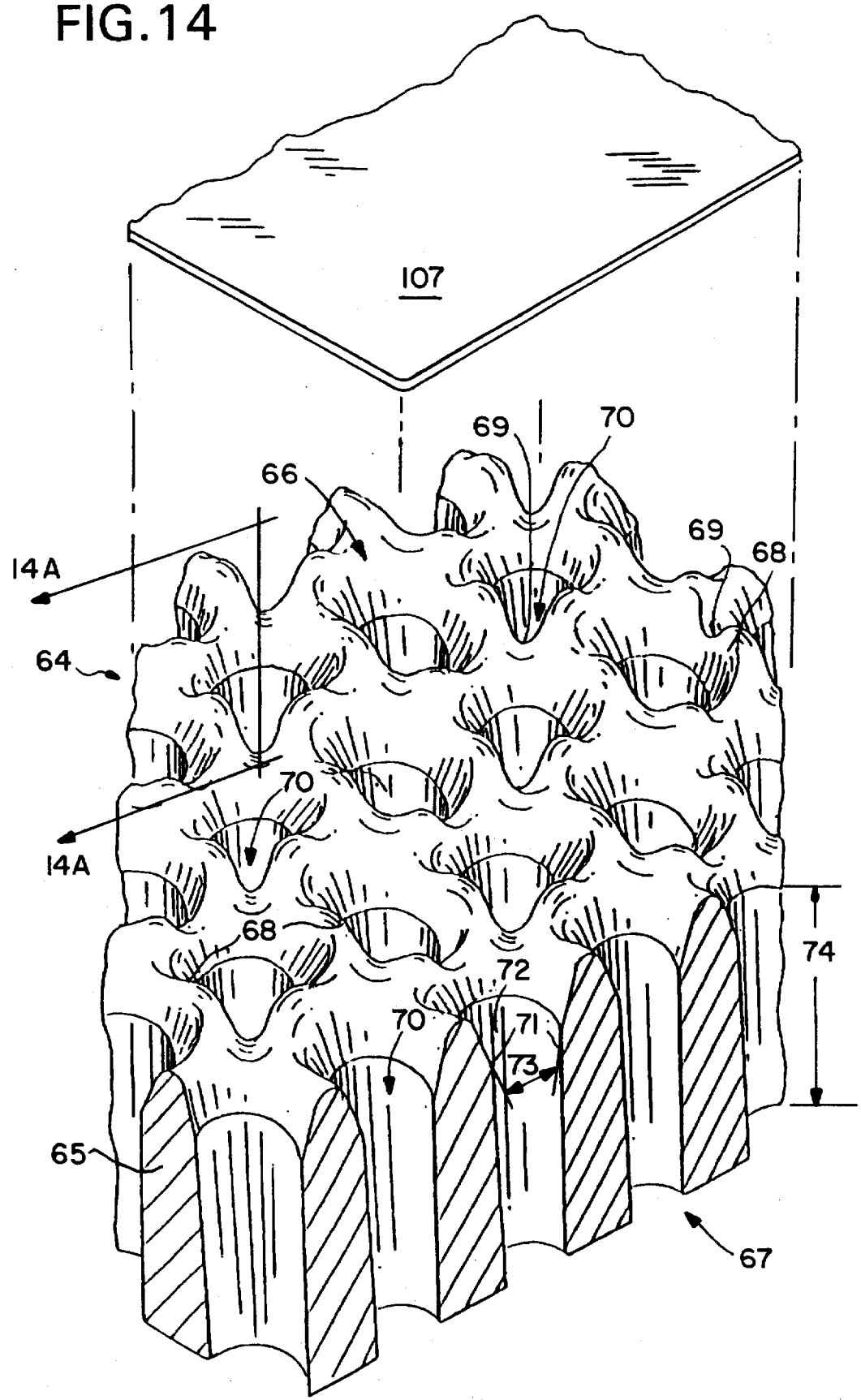
FIG. 14 is an exploded, perspective view of a precursor film and a topographical support surface of a forming sleeve against which the precursor film is forced during processing.

Generally, in a presently preferred form of the process for making the apertured film, portions of a starting film or precursor film are deformed against a cylindrical forming surface or sleeve, a portion of which forming surface is shown in FIG. 14. A generally flat, plate-like forming surface could alternatively be employed in a variation of the process.

Figure 15:
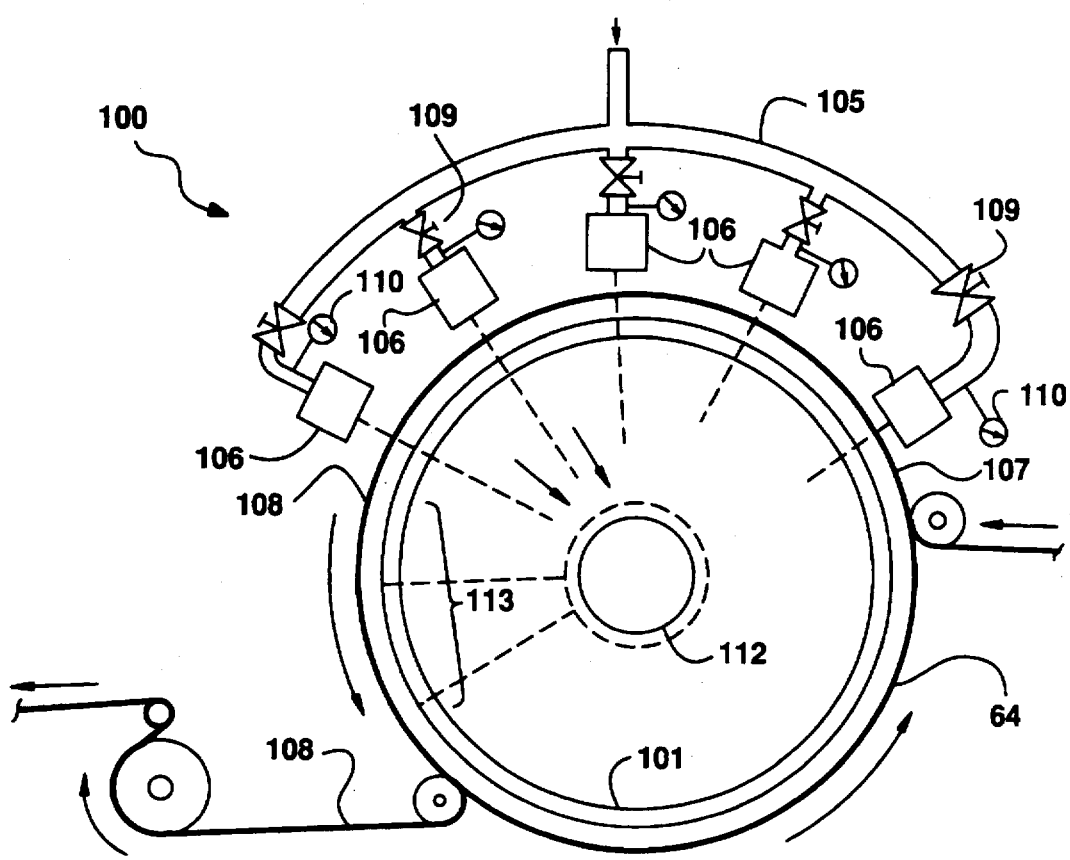
FIG. 15 is a simplified, diagrammatic view of a preferred apparatus for producing an apertured film or web of the present invention.

FIG. 14 illustrates a portion of the hollow cylindrical wall of a topographical forming surface sleeve 64 which can be employed in an apertured film production apparatus 100 as shown in FIG. 15. FIG. 14 shows a precursor film 107 in an exploded, perspective view adjacent the sleeve 64. The precursor film 107 may be embossed or smooth.

The forming surface sleeve 64 may be generally described as having a body or wall 65 which defines a top surface 66 and bottom surface 67. Disposed in a predetermined pattern across top surface 66 is an array of undulating ridges defining peaks 68 separated by valleys 69. A plurality of drainage apertures 70 are arranged in a pattern throughout the sleeve 64. The drainage apertures 70 are tapered or "bell mouthed." The apertures 70 have a larger diameter at the sleeve top surface 66 than at the sleeve bottom surface 67.

Each aperture 70 is surrounded by six adjacent apertures 70. If all of these apertures 70 have a sufficient taper to create diameters greater than their respective center-to-center spacing, each aperture 70 will have six intersections with its neighboring apertures, and these intersections will produce six valleys 69. Depending on their depth, these valleys 69 can either intersect the top surface 66, resulting in the valleys 69 being separated by small plateaus, or the valleys can intersect each other so as to define a peak 68 at the intersection. In this embodiment, each drainage aperture 70 is surrounded by a cluster of six peaks 68 and six valleys 69.

Figure 14A:
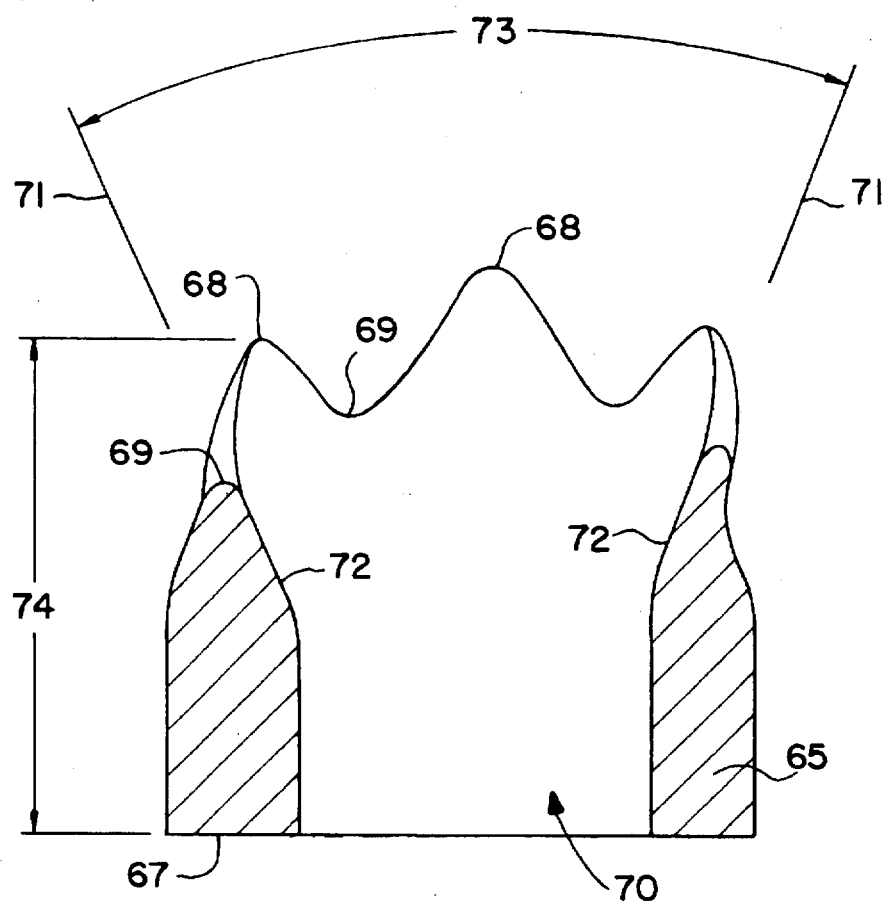
FIG. 14A is a greatly enlarged, fragmentary, cross-sectional view taken generally along the plane 14A—14A in FIG. 14.

Lines 71 can be drawn tangent to opposed points on walls 72 at a distance below the top surface 10 66 that is equal to one hole radius to define an angle 73 (FIGS. 14 and 14A). The angle 73 can be controlled relative to the thickness 74 of the support member 64. A suitable angle 73 can be established without undue experimentation. If the angle 73 is too great, the apertures 70 will be too small and insufficient drainage will be provided. If the angle 73 is too small, there will be very few, or no, peaks and valleys.

An appropriate center-to-center spacing of adjacent apertures 70 in the repeating pattern is provided so that the peaks 68 and valleys 69 are created by the intersection of the tapered, somewhat conical, apertures 70. If the center-to-center spacing of the apertures 70 was greater than the major diameter of the aperture 70 at the top surface 66, then no intersection would result, and the sleeve 64 would have a smooth, flat, top surface 66 with conical apertures 70 disposed throughout. When the center-to-center spacing of adjacent apertures 70 is less than the aperture diameter measured along that center-to-center line, the conical surfaces intersect forming the valleys 69.

The forming sleeve 64 has an outside diameter typically in the range from about 2 feet to about 6 feet, a length typically in the range from about 2 feet to about 16 feet, and a nominal wall thickness of about 0.25 inch. The sleeve 64 is typically made from an acetal polymer. Acrylic may also be used.

A preferred apparatus for making apertured films of the present invention is designated by reference number 100 in FIG. 15, and the apparatus 100 includes a rotatable drum 101. The drum 101 has a honeycomb structure to allow for the passage of fluids therethrough. The drum 101 rotates in a counterclockwise direction (as viewed in FIG. 15).

The forming sleeve 64 is mounted on the drum 101. Disposed about a portion of the periphery of the drum 101 (and sleeve 64 mounted thereon) is a manifold 105 connecting a plurality of orifice strips 106 for directing jets of water against the film 107 carried on the outer surface of sleeve 64. Each orifice strip 106 comprises a row of very small, uniform, circular holes or orifices. The diameter of these holes typically ranges from about 0.005 inch (0.0127 cm) to about 0.010 inch (0.0254 cm). There may be as many as 50 or 60 holes per lineal inch or more if desired.

Water is directed under pressure through the orifices to form columnar streams which impinge on the upper surface of the starting film 107 in a contact zone or aperturing zone below the orifice strips. The distance from the orifice strips 106 to the upper surface of film 107 being processed is about 0.75 inch (1.90 cm). The pressure of the water supplied to the orifice strips 106 is controlled by pressure control valves 109, the pressure being indicated by pressure gauges 110.

The drum 101 is connected to a pump 112 to which a vacuum may be applied to aid in removing water so as to keep the aperturing zone from flooding.

In operation, the starting film 107 is passed around the sleeve 64 in the counterclockwise direction (as viewed in FIG. 15) under the water ejecting orifice strips 106. As the film 107 passes beneath the orifice strips 106, the film 107 is formed into the apertured film 108 of the invention. Residual water is removed 5 from the film by directing a stream of air against it before the film is wound on a spool as the finished apertured film 108 of the invention.

The result of this process is that the film deforms toward the forming surface sleeve 64 and acquires a three-dimensional configuration generally in conformation with some or all of the structural elements of the sleeve. The resulting apertured film 108 has drape and feel characteristics that are generally similar to conventional, woven, tricot-type fabrics.

The specific forming surface configuration of the sleeve 64 can be produced by means of a laser drilling or laser engraving process. The laser engraving process can be controlled to produce the desired contours, hole sizes, spacing, etc. As described hereinafter in detail, a number of embodiments of the apertured web or film of the present invention have been produced with a number of different forming surfaces which can be manufactured with the laser engraving process by varying the appropriate engraving process parameters as described hereinafter in detail.

Figure 16:
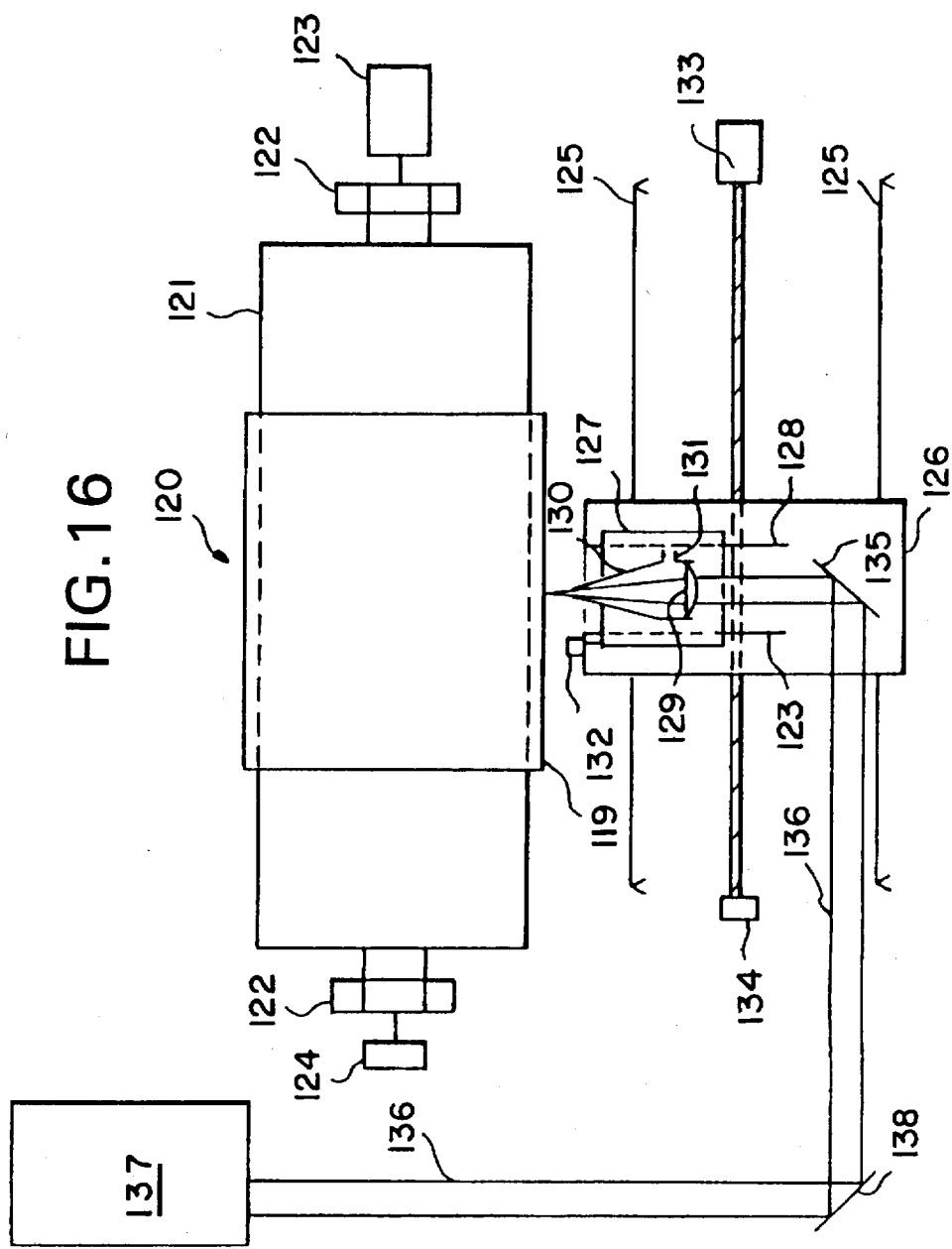
FIG. 16 is a simplified, diagrammatic illustration of an apparatus for producing a topographical support surface sleeve which can be employed in the apparatus illustrated in FIG. 15.

FIG. 16 illustrates a laser engraving apparatus for producing a forming sleeve, such as the above-described sleeve 64. A smooth, annular cylinder made of acetal is preferably used as the starting piece or blank to be engraved. The starting blank is preferably a thin wall (e.g., 0.25 inch thick), seamless tube 120 that has been relieved of residual internal stresses.

Tubes manufactured to date for use as forming surface sleeves have outside diameters ranging between 2 and 6 feet, and lengths ranging between 2 and 16 feet.

The starting blank, tubular workpiece, or tube 120 is mounted on an appropriate arbor or mandrel 121 which fixes the tube 120 in a cylindrical shape and allows rotation about its longitudinal axis in bearings 122. A rotational drive 123 is provided to rotate the mandrel 121 at a controlled rate. A rotational pulse generator 124 is connected to, and monitors, rotation of the mandrel 121 so that its precise radial position is known at all times.

Mounted parallel to, and adjacent, the mandrel 121 is one or more guideways 125 supporting a carriage 126 for movement along the entire length of a mandrel 121 while maintaining a constant clearance with respect to the top surface 119 of tube 120. A carriage drive 133 moves the carriage 126 along the guideways 125, while a carriage pulse generator 134 registers the lateral position of the carriage 126 with respect to the workpiece or tube 120.

A focusing stage 127 is mounted in focus guideways 128 on the carriage 126. The focusing stage 127 allows motion orthogonal to that of the carriage 126 and includes a focusing means or lens 129 for focusing laser energy relative to the top surface 119 of tube 120. A focus drive 132 is provided to position the focusing stage 127 to focus the laser beam through lens 129.

The lens 129 is mounted in a nozzle 130 on the focusing stage 127. The nozzle 130 has means 131 for introducing a pressurized gas into the nozzle 130 for cooling and maintaining cleanliness of lens 129.

Also mounted on the carriage 126 is final bending mirror 135 which directs the beam 136 from a laser 137 to the focusing lens 129.

The laser 137 is located remotely from the mirror 135, with an optional beam bending mirror 138 employed to direct the beam 136 to final beam bending mirror 135. While it would be possible to mount the laser 137 directly on the carriage 126 and eliminate the beam bending mirror 138, space limitations and utility connections to the laser 137 typically make remote mounting preferable.

While a variety of lasers could be used, the preferred laser 137 is a fast flow $CO_2$ laser capable of producing a beam rated at up to 2500 watts. However, sleeve-forming surfaces have been successfully drilled with a slow flow $CO_2$ laser limited to 50 watts.

When the laser power is switched on, the emitted beam 136 is reflected first off of the beam bending mirror 138, and then off of the final beam bending mirror 135 which directs the beam to lens 129. The path of the laser beam 136 is aligned such that it is directed toward an intersection with the longitudinal center line of mandrel 121 and at a right angle to the centerline.

With the lens 129 in position, the beam 136 is focused below, but near, the top surface 119 of tube 120. Focusing the beam 136 below the top of the surface 129 may be described as "defocusing" the laser beam relative to the surface of the tube.

The focusing lens 129 refracts the beam 136 and concentrates the energy near the center of the beam. The power distribution of the resultant focus is highest at the center of the beam and tapers off at the edges in a Gaussian distribution. The rays are not refracted to, or through, a single point, but rather are refracted to a small diameter spot. The spot of smallest diameter at the tube surface is produced when the beam is in focus at the tube surface i.e., at the focal point of the lens at a distance from the lens identified as the focal length. At distances either shorter or greater than the focal length, measured spot sizes will be greater than the minimum.

The sensitivity of the beam focus to the position of the lens relative to the tube surface is inversely proportional to the lens focal length. Minimum spot size is directly proportional to focal length. Therefore, a short focal length lens can produce a small spot size but must be more accurately positioned and is affected dramatically by surface runout. Longer focal length lenses are more forgiving of target positioning, but can only produce somewhat larger spot sizes. Thus, in addition to the power distribution contributing to the tapered top portion of the drilled aperture in the tube or sleeve, the defocusing of the beam below the surface also contributes to the angle and length of the taper, and hence the shape and size of the peaks and valleys.

In order to fabricate a support sleeve (e.g., such as the above-disclosed sleeve 64) from a blank tube 120, an initial focusing step must be performed to determine a reference surface position. With the blank tube 120 on the mandrel 121, the laser 137 is pulsed briefly. The mandrel 121 is rotated slightly between pulses such that a series of small depressions is produced in the tube 120. The focusing stage 127 is then moved with respect to the mandrel center line to change the focus position and another series of depressions is produced. Typically, a matrix of 20 rows of 20 depressions each is drilled, and the focusing stage position for each row is recorded. The depressions are examined microscopically, and the row of smallest diameter depressions is identified. The smallest diameter depressions are produced when the beam is focused on the top surface 119 of the blank tubular workpiece 120. Thus, the recorded position of the focusing stage 127 at which the smallest diameter depressions were produced is taken as a "reference position" corresponding to the focus of the beam on the top surface of the workpiece 120. During subsequent operation of the system to engrave the workpiece 120, the focusing stage 127 is moved toward the workpiece surface 119 so as to move the focal point of the laser beam to a predetermined position below the workpiece surface. (This has the effect of defocusing the beam at the workpiece surface.)

Figure 17:
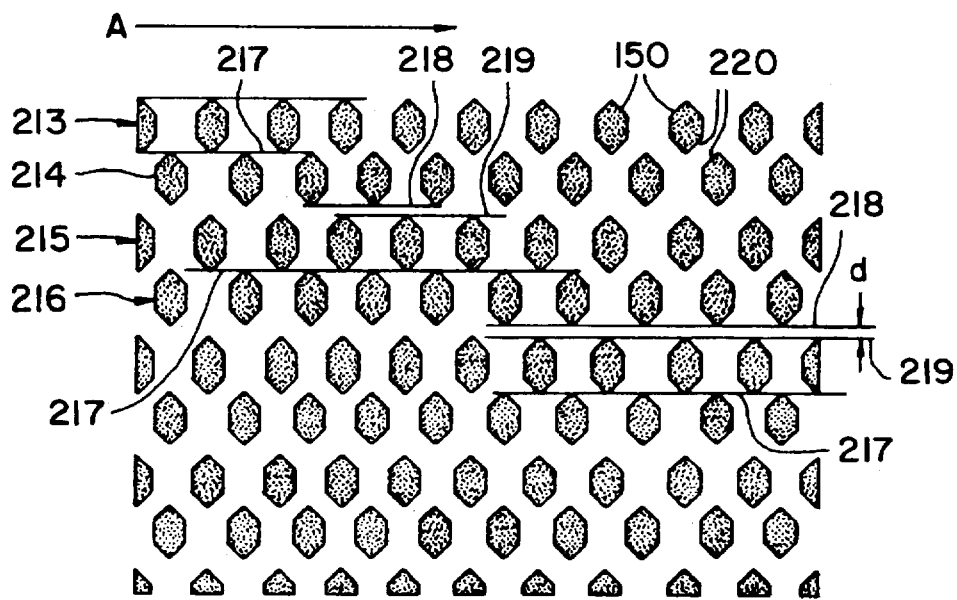
FIG. 17 is a bit map of instructions for a computer-operated laser apparatus of the type illustrated in FIG. 16, and the bit map represents a pattern of apertures to be engraved or drilled in a workpiece to form the topographical support surface illustrated in FIG. 14.

A desired surface configuration can be drilled or engraved with the laser in the above-described apparatus by controlling the process with a computer to follow a pattern. FIG. 17 illustrates such a pattern or bit map which can be employed to engrave the type of forming surface illustrated in FIG. 14 described above.

Referring now to the bit map illustrated in FIG. 17, the forming sleeve apertures 70 are represented as hexagons 150 in a nested array. Other shapes, such as, for example, circles, squares, octagons, or irregular shapes, or combinations thereof, may be used, depending on the desired topographical configuration. Such a repeating pattern is provided with the number of repeats that will be required to cover the circumference of the tube 120 and complete the surface without an obvious seam. Similarly, the advance along the longitudinal axis of the tube 120 per repeat and total number of repeats is established. These data are entered into a computer control for operating the laser drilling machine.

In FIG. 17, the hexagons 150 define two top rows 213 and 214. The rows 213 and 214 run parallel to a directional arrow A in FIG. 17. The hexagons 150 are 7 pixels wide, 11 pixels long, and within each row are spaced 8 pixels apart. Row 213 of the hexagons is spaced closely to row 214 of the hexagons. Specifically, as can be seen in FIG. 17, the lower tip of each hexagon in row 213 is tangent to a line 217, which line 217 is also tangent to the upper tip of each hexagon in row 214. Rows 215 and 216 duplicate the pattern and spacing of rows 213 and 214. The spacing between rows 215 and 216 corresponds substantially to the above-mentioned spacing between rows 213 and 214. Row 215, however, is spaced from row 214. As seen in FIG. 17, the lowermost tips of the hexagons in row 214 are tangent to line 218, while the uppermost tips of the hexagons in row 215 are tangent to line 219. Lines 218 and 219 are spaced from each other by a distance d, which in the pattern illustrated in FIG. 17 is 3 pixels. The above-described pattern of the rows 213, 214, 215, and 216 is repeated throughout the bit map of FIG. 17. It will be understood that, in other design variations, the spacing of the hexagons may be non-uniform within a given row or between adjacent rows.

The distance between parallel adjacent walls 220 of two adjacent hexagons shown in the bit map of FIG. 17 is selected so that, inter alia, the sleeve body 65 has sufficient strength to resist the fluid forces and to allow normal handling.

To engrave the pattern, the mandrel 121, with the tubular workpiece 120 mounted thereon, is rotated in front of the lens 129. The carriage 126 is positioned by the motor drive 133 so that the first aperture position corresponds with the focal point of the lens 129. Then the focusing stage 127 is moved inwardly by drive 132 to locate the focal point inside the interior of the top surface 119 to be drilled. The laser 137 is then pulsed, with some combination of pulse power level and duration.

As seen in FIG. 14A, the diameter of aperture 70 at the top surface 66 is considerably larger than the diameter of the aperture at the lower surface 67. In order to achieve the desired topographical configuration, two factors are measured and controlled: (1) the depth to which the lens 129 is focused into the interior of the tubular workpiece (e.g., increasing the depth of the cone angle 73), and (2) the power level or pulse duration (e.g., increasing either one increases the depth and diameter of the aperture 70). Once an aperture 70 of the proper diameter and taper is achieved, the mandrel rotational drive 123 and carriage drive 133 are indexed to reposition the workpiece 120 such that the next intended hole position corresponds to the focal point. The process is then repeated until the entire pattern has been drilled. This technique is known as "percussion" drilling.

If the laser selected is of sufficient power, the mandrel 121 and carriage 126 do not need to be stopped during the laser pulse. The pulse can be of such short duration that any movement of the workpiece during the drilling process is inconsequential. This is known in the trade as "fire-on-the-fly" drilling.

If the laser can recover rapidly enough, the workpiece 120 can be rotated at a fixed speed and the laser pulsed once to create each hole. For a forming surface pattern such as the one shown in FIG. 14, the laser 137 would normally be pulsed to produce a complete column of apertures, the carriage 126 indexed to the next column position, and the laser 137 pulsed for the next column of apertures.

One problem that may occur depending on the type of material and density of the pattern of apertures, is the introduction of a large amount of heat into a small area of the forming surface. Gross distortion, and the loss of pattern registration may result. Under some conditions, major dimensional changes of the part could occur, and the resulting forming surface would not be correct. In extreme cases, the tube may crack.

Figure 18:
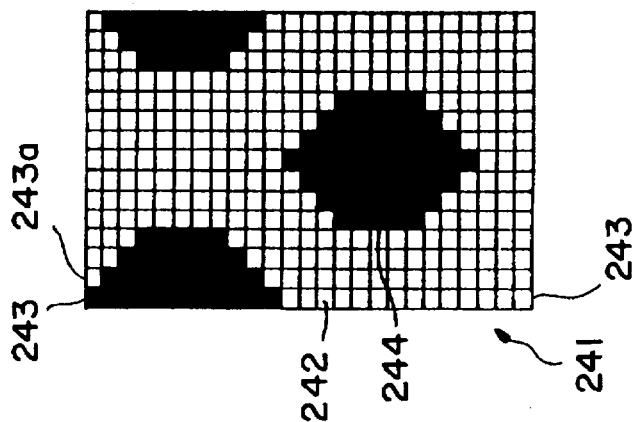
FIG. 18 is a simplified diagrammatic illustration of the smallest rectangular repeat element, 25 pixels long by 15 pixels wide, of the pattern shown in FIG. 17.

In a preferred form of the engraving process this problem is eliminated by employing a defocused raster scan drilling technique. With this technique, the pattern is reduced to the smallest rectangular repeat element 241 as depicted in FIG. 18. This repeat element contains all of the information required to produce the pattern in FIG. 17. When these elements are used like tiles and placed both end-to-end and side-by-side, the proper overall pattern results.

This repeat element is further divided into a grid of smaller rectangular units or "pixels" 242. Though each pixel 242 is typically square, for some purposes it may be more convenient to employ pixels of unequal proportions. A typical square pixel size is 0.05 mm. by 0.05 mm.

Each column of pixels 242 represents one pass of the workpiece past the focal position of the laser. This column is repeated as many times as is required to extend completely around tubular workpiece 120 as the workpiece 120 is rotated through one revolution (typically at a rate at which the speed of the surface 119 is 20.3 meters/minute regardless of the diameter of the workpiece). Each pixel 242 in FIG. 18 where the laser is intended to be switched on to create a hole is black. Those pixels where the laser is switched off are white.

To begin drilling at the top of the first column of pixels 243 in FIG. 18, while the mandrel is turning at a constant rate, the laser 137 is turned on, maintained at a constant power level for 11 pixels 242, and then switched off. These pixels are counted by the rotational pulse generator 124 (FIG. 16). The laser 137 remains off for the next 14 units or pixels 242. This laser off/on sequence is repeated for the first revolution, at which point the mandrel 121 has returned to its initial rotational position, the carriage drive 133 has repositioned the carriage 126 one unit or pixel to the next adjacent column 243a of pixels 242. The apparatus is then ready to begin engraving column 243a.

During the engraving of column 243a, the laser 137 has a shorter "on time" (now 9 units) and longer "off time" (now 16 units). The total of on and off times in a repeat unit is a constant based on the pattern height.

This process is repeated until all of the columns have each been processed over an entire revolution. In the case of the element 241 FIG. 18 with 15 columns of pixels 242, 15 revolutions of the mandrel 121 are required. At the end of the fifteenth column, the process returns to the instruction map in column 243.

In this approach, each pass produces a number of narrow cuts in the material, rather than a large hole. Because these cuts are precisely registered to line up side-by-side and overlap somewhat, the cumulative effect is a series of holes. In the pattern in FIG. 18, each column of hexagonal elements 244 actually requires 7 passes separated by one unengraved, complete revolution, and this distributes the energy around the tube 120 to minimize local heating.

If, during this drilling operation, the lens 129 was focused right at the top surface 119 of the sleeve material, the result would be hexagonal holes with reasonably parallel walls. The combination of raster scan drilling with the "defocused" lens technique, however, produces the forming surface of the type illustrated in FIG. 14. Typically, the holes or apertures 70 are quite small and numerous. Typical patterns range from 800 to 1400 apertures per square inch.

Figure 19A:
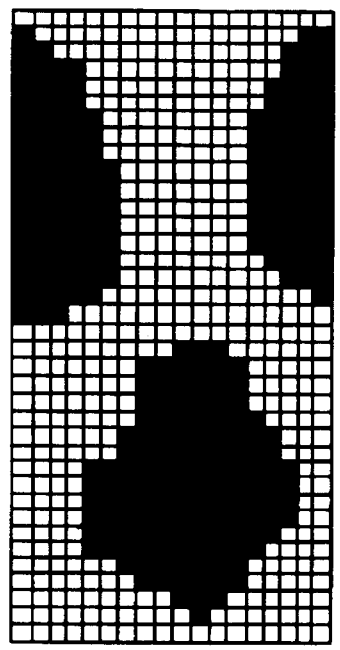
FIG. 19A is a simplified diagrammatic illustration of the smallest rectangular repeat element of the pattern shown in FIG. 19.
Figure 19:
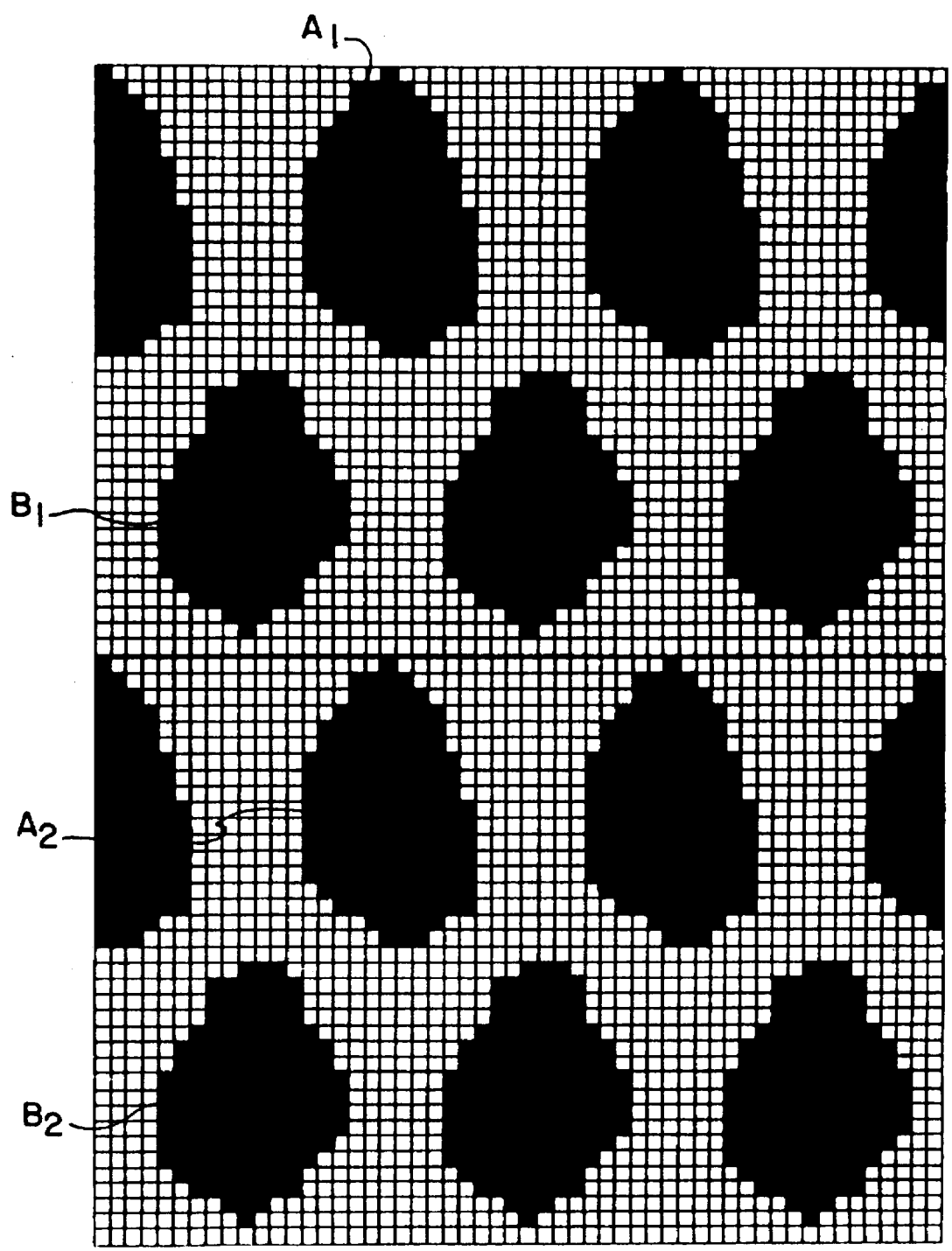
FIG. 19 is a bit map, similar to the one illustrated in FIG. 17, for a different set of laser operating instructions.

FIG. 19 is another pixel-by-pixel representation of an on/off laser power pattern programmed into the computer control. The pattern consists of repeating pairs of rows of elements labeled $A_1, B_1, A_2, B_2$, etc., which represent the holes or apertures in the forming surface sleeve. The elements $A_1$ have a first irregular shape, and the elements $B_1$ have a second irregular shape. A tubular workpiece was engraved according to this pattern using the laser drilling apparatus illustrated in FIG. 16 to provide the forming sleeve surface configuration shown in FIGS. 20 and 21. The tubular workpiece was approximately 3 feet in diameter, 12 feet long, and 6 mm thick. The laser drilling process took about 7 days to complete.

Figure 20:
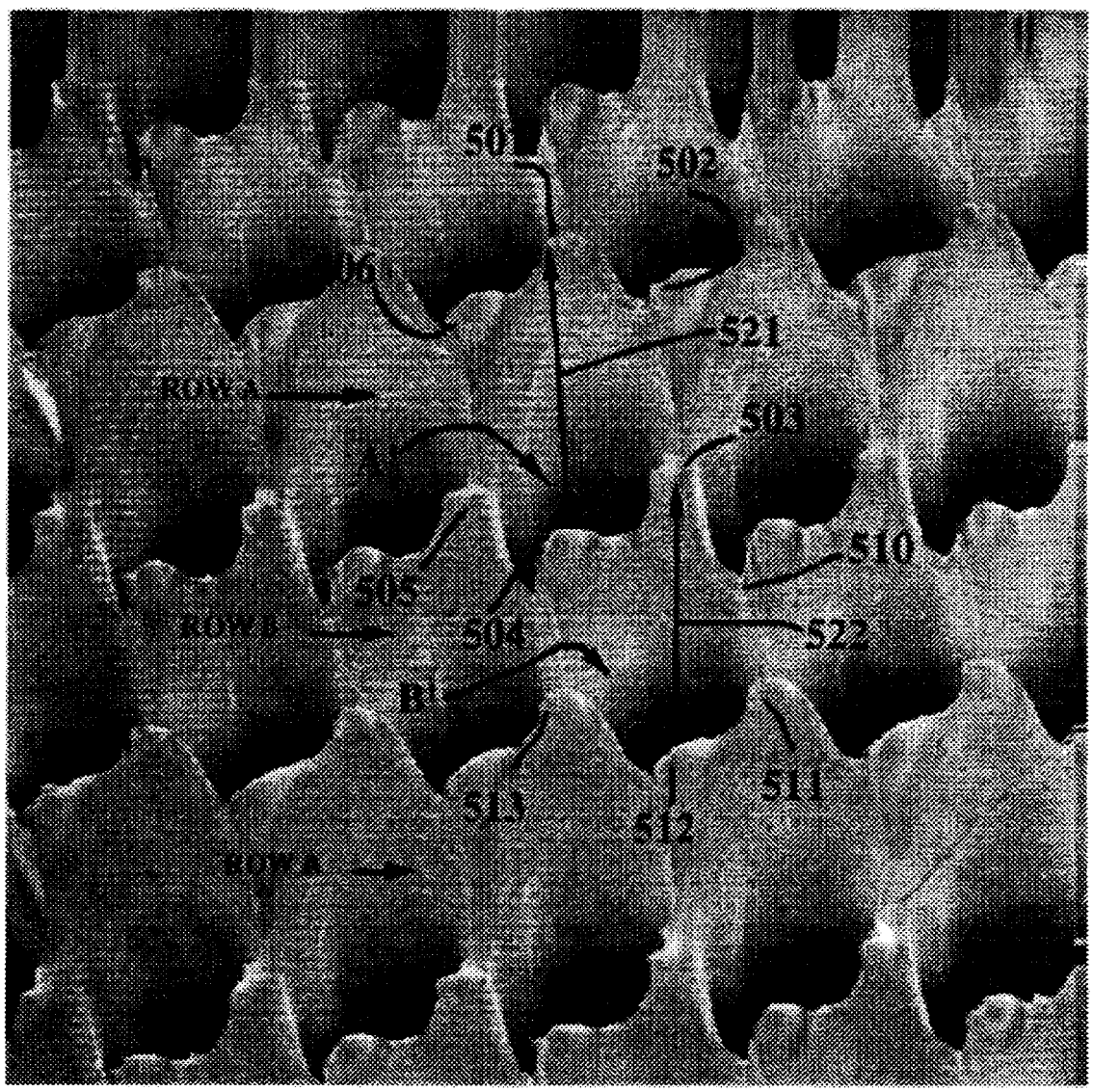
FIG. 20 is digitized scanning electron microscope image of a portion of the forming surface produced according to the bit map illustrated in FIG. 19.

In FIG. 20, the illustrated forming surface includes first row A of apertures (seen in the upper part of FIG. 20), a next adjacent row B of apertures, and a second row A of apertures below row B of apertures. The first row A of apertures includes aperture A'. The next adjacent row B of apertures includes aperture B' which is adjacent to aperture A'.

The upper portion of aperture A' is surrounded and defined by peaks 501, 502, 503, 504, 505, and 506. The upper portion of aperture B' is surrounded and defined by peaks 510, 511, 512, 513, 504, and 503. It will be recognized that peaks 504 and 503 are common to both of apertures A' and B'. The double arrowhead line extending between peaks 501 and 504 represents the major diameter of the upper portion of aperture A'. The major diameter 521 was 0.085 inch in the actual forming sleeve that was produced. Similarly, line 522 extending between peaks 503 and 512 represents the major diameter of the upper portion of aperture B'. The major diameter was 0.075 inch in the actual forming sleeve that was produced.

The various other peak-to-peak distances associated with aperture A' in the support member forming surface are set forth in Table A. The various peak-to-peak distances associated with aperture B' are set forth in Table B.

TABLE A

| | (Dimensions In Inches) | | | | |
|---|---|---|---|---|---|
| PEAK NO. | 501 | 502 | 503 | 504 | 505 |
| 501 | — | — | — | — | — |
| 502 | 0.037 | — | — | — | — |
| 503 | 0.067 | 0.040 | — | — | — |
| 504 | 0.085 | 0.067 | 0.037 | — | — |
| 505 | 0.070 | 0.075 | 0.055 | 0.035 | — |
| 506 | 0.035 | 0.056 | 0.065 | 0.065 | 0.040 |

TABLE B

| | (Dimensions In Inches) | | | | |
|---|---|---|---|---|---|
| PEAK NO. | 510 | 511 | 512 | 513 | 503 |
| 510 | — | — | — | — | — |
| 511 | 0.037 | — | — | — | — |
| 512 | 0.062 | 0.035 | — | — | — |
| 513 | 0.065 | 0.056 | 0.037 | — | — |
| 503 | 0.035 | 0.066 | 0.075 | 0.063 | — |
| 504 | 0.055 | 0.067 | 0.055 | 0.037 | 0.037 |

Figure 21:
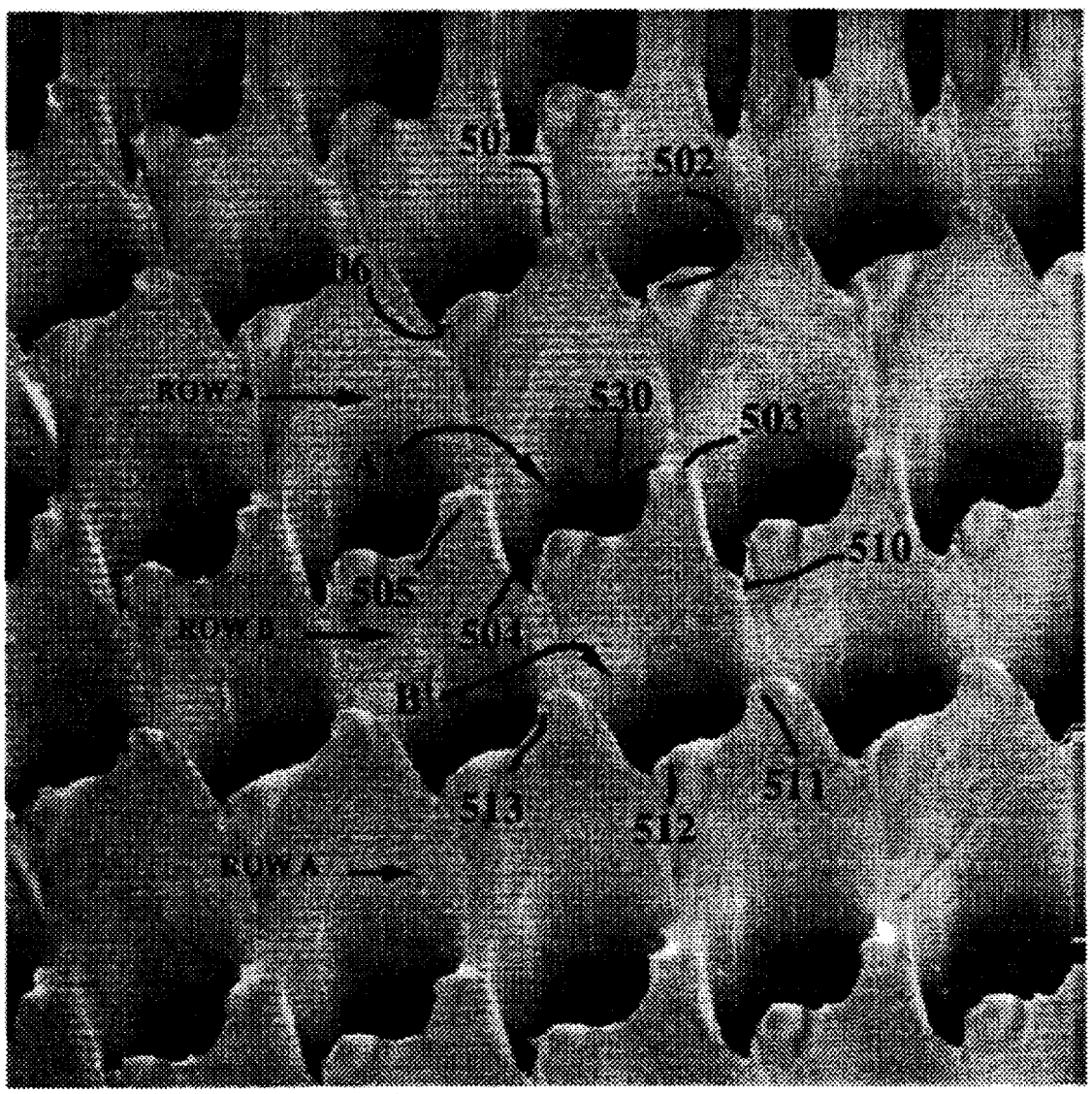
FIG. 21 is the same digitized image shown in FIG. 20, but FIG. 21 includes an additional reference number.

FIG. 21 is the same digitized image as that shown in FIG. 20 but it has been marked and numbered to show the distance between the bottom of a valley between two adjacent peaks and a line connecting the same two peaks. For example, line 530 in FIG. 21 connects peaks and 504 associated with aperture A'. The depths of the valleys between peaks 501-506 associated with aperture A' are shown in the upper portion of Table C. The depths of the two valleys associates with aperture B' (i.e., the valley between peaks 510 and 511 and the valley between peaks 504 and 513) are shown in the lower portion of Table C. The valleys between the remaining peaks associated with aperture B', those between peaks and 512, and between 512 and 513, are structurally analogous to those valleys between peaks 501 and 506, and 501 and 502, respectively.

TABLE C

| Valley Between Peaks | Valley Depth Inches |
|---|---|
| 501 and 502 | 0.016 |
| 502 and 503 | 0.020 |
| 503 and 504 | 0.024 |
| 504 and 505 | 0.025 |
| 505 and 506 | 0.020 |
| 506 and 501 | 0.012 |
| 510 and 511 | 0.026 |
| 504 and 513 | 0.026 |

Figure 22:
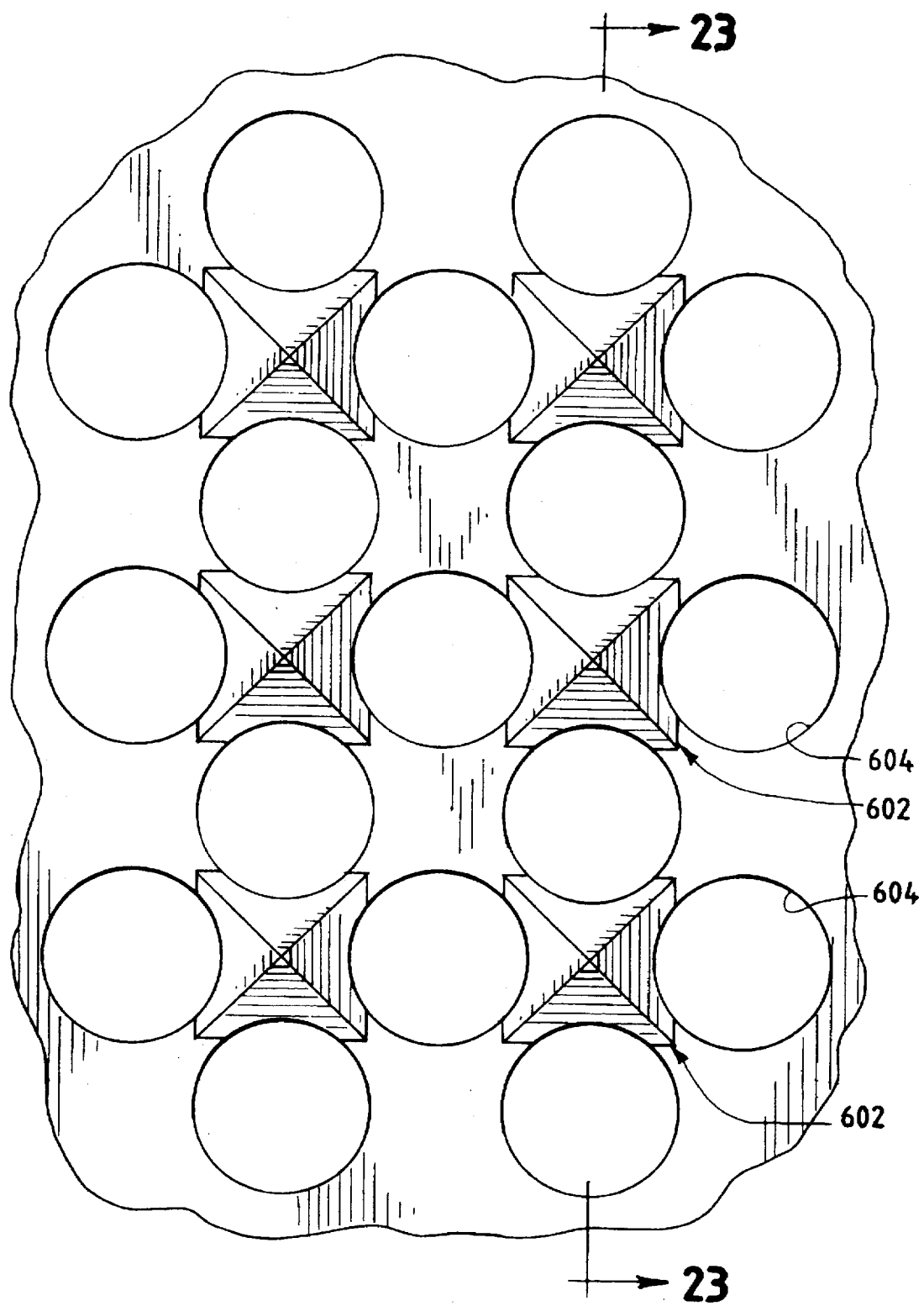
FIG. 22 is a fragmentary, enlarged, plan view of a forming surface which includes pyramid-shaped projections.
Figure 23:
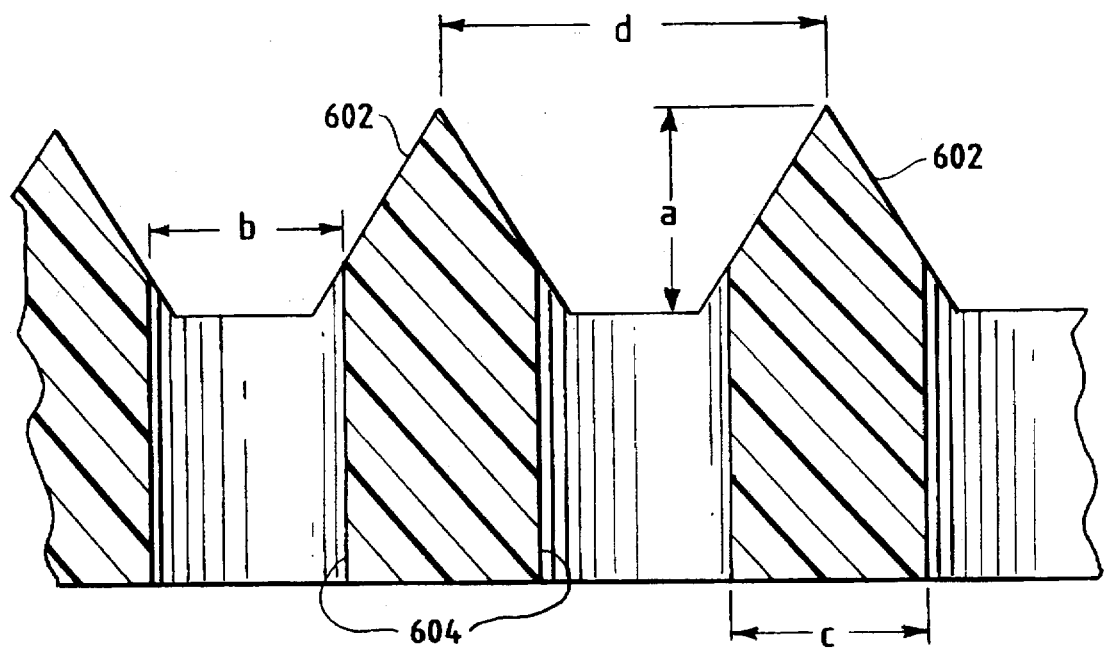
FIG. 23 is a fragmentary, cross-sectional view taken generally along the plane 23—23 in FIG. 22.

Another forming surface, which can be used to produce webs of the present invention, is illustrated in FIGS. 22 and 23. This forming surface can be produced via a number of methods, including conventional machining techniques. The forming surface has equally spaced rows and columns of pyramids 602 projecting from a flat surface defining cylindrical drain holes 604. The drain holes 604 are arranged in equally spaced rows and columns. The spacing between the pyramids 602 in each row and in each column is uniform. The spacing between the holes 604 in each row and in each column is uniform. The alternate rows and columns of the holes 604 are staggered or offset symmetrically relative to the adjacent rows and columns of holes, respectively. A portion of each side of each pyramid 602 is intersected and cut away by an adjacent hole 604.

Forming surfaces of the various types described above may be used to produce the apertured film or web of the present invention from a suitable precursor film. According to an aspect of the present invention, the precursor film in which the apertures are formed has particular characteristics which include, among others, significant elasticity with relatively high toughness and strength. After forming the apertured web or film from the precursor film, the preferred form of the apertured web or film has a breathability and flexibility with an elasticity accommodating a stretch elongation of at least 50% and a recovery of greater than 65% from a stretch elongation of 50%. Preferably, the apertured web or film has an elasticity such that a tension force within the range of about 0.5 to about 2.5 pounds per inch of web transverse to the tension force will produce a 50% stretch elongation with a recovery of at least 65%.

A preferred form of precursor film is a solid film which includes a copolymer of ethylene and a comonomer polymerized in a polymer structure using a single-site metallocene-type polymerization catalyst. The polymer structure may be a block and branched structure. The comonomer preferably comprises styrene, ethylenically unsaturated olefin(s) having from 3 to about 20 carbon atoms, or combinations thereof. One suitable type of copolymer is the linear ethylene/butene copolymer sold under the trademark EXACT 3026 by the Exxon Chemical Company, which has an office at 351 North Oakwood Road, Lake Zurich, Ill. 60047-1562, U.S.A. Such copolymers are described in the U.S. Pat. No. 5,322,728, and the disclosure of that patent is incorporated herein by reference to the extent pertinent and to the extent not inconsistent herewith.

One suitable type of precursor film incorporating such a copolymer is that sold by Exxon under the film designation XLP-919. The XLP-919 film includes low density polyethylene with the metallocene catalyzed linear ethylene/butene copolymer sold by Exxon under the trademark EXACT 3026.

There are other suitable metallocene-type catalyzed ethylene-based copolymer films sold by Exxon Chemical Company. These include the following films: the film designated XLP-940 which includes as components low density polyethylene and the Exxon Chemical Company linear ethylene/hexene copolymer sold under the trademark EXACT 3030; the film designated XPC-052 is a coextruded film which includes as components ethylene-vinyl acetate polymer and the Exxon Chemical Company linear ethylene/butene copolymer sold under the trademark EXACT 3026; the film designated XLP-980 which includes as components low density polyethylene and the Exxon Chemical Company linear ethylene/butene copolymer sold under the trademark EXACT 3028; the film designated XLP-981 which includes as components low density polyethylene and the Exxon Chemical Company linear ethylene/butene copolymer sold under the trademark EXACT 3025; and the film designated XLP-988 which includes as components low density polyethylene and the Exxon Chemical Company linear ethylene/butene copolymer sold under the trademark EXACT 3028 in 1:1 combination with the copolymer sold under the Exxon Chemical Company trademark EXACT 3035. These films also include additives to provide color and other characteristics, with the concentration of each of such other additives in the film being about 5% or less.

It is also contemplated that other suitable films may include those comprising metallocene-polymerized polyethylene-based plastomer blends with conventional polyethylene resin, metallocene-polymerized polyethylene-based plastomer blends or coextrudates with ethylene vinyl acetate or ethylene methyl acrylate.

The precursor films can be either cast or blown. Preferably, the metallocene-catalyzed ethylene-based copolymer contained in the precursor film has a density in the range of about 0.86 to about 0.95 g/cm³, a molecular weight distribution in the range from about 1.0 to about 3.50, and a melt index in the range from about 1.0 to about 3.0 g/10 min.

The precursor film is preferably processed as described above to form apertures and other deformations so that the resulting web or film exhibits the desired characteristics. A preferred precursor film has a thickness ranging from about 1 to about 4.5 mils, preferably between about 2 to about 3 mils.

A preferred apertured web or film has a thickness in the range of about 2.25 to about 30 mils (preferably about 6 to about 12 mils) and has a basis weight in the range of about 0.7 to about 4.5 oz/yd² (preferably about 1.0 to about 2.0 oz/yd²).

The preferred apertured web or film has an elasticity accommodating at least a 50% stretch elongation when subjected to a tension force in the range of about 0.5 (preferably 1) to about 2.25 (preferably 2) pounds per inch of film, a recovery of at least 70% for a 50% stretch, and a ratio of recovery energy to stretch energy multiplied by 100 that is greater than 25 (preferably greater than 40) for a 50% stretch elongation.

Preferably, the apertured film has an elongation at break in the range of about 200 to about 500% when the film is elongated in either the machine direction or in the cross direction. Preferably, the tensile strength at break is greater than 2 pounds per inch of film. The preferred range is about 2 to about 7 pounds.

The apertured film has a Frazier air permeability of about 20 to about 300 cubic feet per minute per square foot, and in some applications the preferred range 50 to 75 cubic feet per minute per square foot.

The apertured film preferably has irregularly shaped apertures or holes. The average hole size, expressed as an equivalent circular diameter ("ECD") is in the range of about 0.1 to about 100 mils. In some applications, the preferred range is from about 1.0 to about 10 mils with about 80% of the holes having an equivalent circular diameter of less than 15 mils.

The open area of the apertured film is in the range of about 0.5 to about 20 percent, and in some applications, a more preferred range is from about 1 to about 3 percent.

Further, in some applications, the film has an equivalent circular diameter (ECD) COV in the range of about 18 to about 79%.

The apertured film has a moisture vapor transfer rate greater than about 300 g/m²/24 hrs., and preferably greater than about 2000 g/m²/24 hrs.

Several sample backing webs were produced. The following Tables 1, 2, and 3 set forth information regarding the materials, processing conditions, and chemical and physical properties. The examples are set forth for purposes of illustration.

In these examples, the precursor film was formed into apertured film using the process and type of apparatus described above with reference to FIG. 15 (wherein the precursor film is deformed using columnar water jets to apply force to the film while it is supported on a three-dimensional forming surface).

A variety of forming surfaces have been used in the examples, and these are identified by arbitrary letter designations A, B, C, D, E, F, and G in the Tables 1, 2, and 3. The designations A–F correspond to forming surfaces produced by the process described above with reference to FIG. 16. Forming surface G is depicted in FIGS. 22 and 23 and is further described hereinafter.

The forming surfaces A–F were engraved by a 1300 watt laser having a positive meniscus lens with a 5 inch focal length and employing a 0.05 mm.×0.05 mm. square pixel size. The surfaces A–F were engraved according to the preferred defocused raster scan drilling technique described above. The forming surfaces A–F in each case are acetal and were rotated on a mandrel at a 20.3 meters/minute surface speed (independent of forming surface diameter) with a 0.05 mm. longitudinal carriage advance per each revolution of the mandrel. The laser was operated at peak power of 1300 watts when switched on pursuant to a predetermined bit map and pixel pattern as identified in the following Table D. The laser beam diameter entering the lens was 30 mm., and the beam was focused to a diameter of 200 microns at a focal point below the workpiece at a depth identified in the following Table D. These and other relevant forming surface production parameters for surfaces A–F are set forth in the following Table D.

TABLE D

| FORMING SURFACE DESIGNATION FROM TABLES 1, 2, AND 3 | DISTANCE BELOW INITIAL UNENGRAVED SLEEVE FORMING SURFACE AT WHICH LASER IS FOCUSED | SMALLEST REPEAT LASER BIT MAP INSTRUCTIONS | ELEMENT OF LASER BIT MAP |
| --- | --- | --- | --- |
| A | 3.0 mm. | FIG. 17 | FIG. 18 |
| B | 3.0 mm. | FIG. 17 | FIG. 18 |
| C | 2.5 mm. | FIG. 17 | FIG. 18 |
| D | 3.0 ram. | FIG. 17 | FIG. 18 |
| E¹ | 3.0 mm. | FIG. 19 | FIG. 19A |
| ¹¹F² | 3.0 mm. | FIG. 17 | FIG. 18 |

¹FIGS. 20 and 21 show scanning electron microscope images of the forming surface E.
²Forming surface F was produced by operating the laser to drill the row pattern of openings in an orientation 90° from that shown for the row pattern in FIG. 17.

Forming surface G has the configuration illustrated in FIGS. 22 and 23 with the following dimensions:

a=0.64 mm b=0.34 mm c=0.32 mm d=0.66 mm.

In the examples listed in the following Tables 1, 2, and 3, the film was processed with the specified one of the forming surfaces A–G, and Tables 1, 2, and 3 list the particular film processing parameters, such as water jet orifice size, orifice arrangement, water temperature and pressure, and line speed.

TABLE 1

|  | Example 1 | Example 2 | Example 3 | Example 4 |
| --- | --- | --- | --- | --- |
| Precursor Film |  |  |  |  |
| Film Designations | XLP-919 | XLP-940 | XPC-052 | XLP-980 |
| Film Type | Blend | Blend | Coextruded | Blend |
| Film Composition |  |  |  |  |
| Polymer 1 | EXACT™ 3026 | EXACT™ 3030 | EXACT™ 3026 | EXACT™ 3028 |
| Polymer 2 | LDPE | LDPE | EVA | LDPE |
| Ratio (Polymer 1: Polymer 2) | 80:20 | 80:20 | 80:20 | 80:20 |

TABLE 1-continued

| | Example 1 | Example 2 | Example 3 | Example 4 |
|---|---|---|---|---|
| Thickness (mils) | 2.25 | 2.25 | 2.25 | 2.5 |
| MD Tensile Strength (at break) (lb/in) | 8.82 | 11.67 | 14.65 | 17.8 |
| CD Tensile Strength (at break) (lb/in) | 8.55 | 8.96 | 14.8 | 17 |
| MD Elongation (at break) (%) | 579 | 629 | 544 | 660 |
| CD Elongation (at break) (%) | 696 | 614 | 678 | 800 |
| Polymer 1 Properties | | | | |
| Density of Polymer 1 | 0.908 | 0.907 | 0.908 | 0.901 |
| Molecular Weight Distribution of Polymer 1 | 1.9 | 2.06 | 1.9 | 1.86 |
| Melt Index (g/10 min) of Polymer 1 | 2.8 | 2.2 | 2.8 | 1.17 |
| Web Fabrication Conditions | | | | |
| Forming surface | D | D | D | E |
| Orifice Diameter (mils) | 5 | 5 | 5 | 5 |
| Number of orifices per inch | 50 | 50 | 50 | 50 |
| Number of manifolds | 3 | 3 | 3 | 3 |
| Water Temperature (°F.) | 160 | 160 | 160 | 160 |
| Manifold pressure (psi) | 850 | 1200 | 850 | 1050 |
| Line Speed (ft/min) | 50 | 50 | 50 | 72 |
| Web Properties | | | | |
| MD Tensile Strength (at break) (%) | | | | 4.36 |
| CD Tensile Strength (at break) (%) | 3.2 | 2 | 2.6 | 3.15 |
| % Recovery after 50% CD stretch | 80 | 76 | 84 | 81 |
| Stretch Force at 50% stretch (lb/in) | 1.624 | 0.943 | 1.152 | 1.311 |
| Recovery Energy/Stretch Energy at 50% stretch (× 100) | 48 | 47 | 56 | 50 |
| MVTR after adhesive coating (g/m²/24 hrs) | 5000 | 4000 | | 3000 |
| Frazier Air Permeability (CFM/ft²) | 135 | 45 | 91 | 60 |
| Open Area (%) | 0.91 | 1.5 | 1.53 | 1.51 |
| Average Pore Size, ECD (mils) | 3.77 | 5.22 | 4.41 | 4.46 |
| ECD COV (%) | 49.6 | 49.7 | 58.9 | 53.4 |

TABLE 2

| | Example 5 | Example 6 | Example 7 | Example 8 |
|---|---|---|---|---|
| Precursor Film | | | | |
| Film Designations | XLP-919 | XLP-981 | XPC-988 | XLP-980 |
| Film Type | Blend | Blend | Blend | Blend |
| Film Composition | | | | |
| Polymer 1 | EXACT™ 3026 | EXACT™ 3025 | 1:1 EXACT™ 3025/3028 | EXACT™ 3028 |
| Polymer 2 | LDPE | LDPE | LDPE | LDPE |
| Ratio (Polymer 1: Polymer 2) | 80:20 | 80:20 | 80:20 | 80:20 |
| Thickness (mils) | 3 | 2.7 | 2.5 | 2.5 |
| MD Tensile Strength (at break) (lb/in) | 14.5 | 14.5 | 16.2 | 17.8 |
| CD Tensile Strength (at break) (lb/in) | 13.1 | 13.5 | 15 | 17 |
| MD Elongation (at break) (%) | 730 | 680 | 650 | 660 |
| CD Elongation (at break) (%) | 790 | 740 | 700 | 800 |
| Polymer 1 Properties | | | | |
| Density of Polymer 1 | 0.908 | 0.91 | 0.945 | 0.901 |
| Molecular Weight Distribution of Polymer 1 | 1.9 | 1.95 | 1.9 | 1.86 |
| Melt Index (g/10 min) of Polymer 1 | 2.8 | 1.16 | 1.9 | 1.17 |
| Web Fabrication Conditions | | | | |
| Forming surface | D | A | A | A |
| Orifice Diameter (mils) | 5 | 5 | 5 | 5 |
| Number of orifices per inch | 50 | 50 | 50 | 50 |
| Number of manifolds | 3 | 3 | 3 | 3 |
| Water Temperature (°F.) | 160 | 160 | 157 | 160 |
| Manifold pressure (psi) | 1200 | 1200 | 1050 | 1050 |
| Line Speed (ft/min) | 70 | 70 | 72 | 72 |
| Web Properties | | | | |
| MD Tensile Strength (at break) (%) | 6.4 | 5.67 | 4.59 | 4.14 |
| CD Tensile Strength (at break) (%) | 4.7 | 4.46 | 3.49 | 3.25 |
| MD Elongation (at break) (%) | 379 | 418 | 413 | 340 |
| CD Elongation (at break) (%) | 459 | 472 | 350 | 455 |
| % Recovery after 50% CD stretch (× 100) | | 72 | 77 | |
| Stretch Force | | | 2.023 | 1.56 |

TABLE 2-continued

| | Example 5 | Example 6 | Example 7 | Example 8 |
|---|---|---|---|---|
| at 50% stretch (lb/in) | | | | |
| Recovery Energy/Stretch Energy at 50% stretch (× 100) | | 37 | 43 | |
| MVTR after adhesive coating (g/m²/24 hrs) | 5000 | | | |
| Frazier Air Permeability (CFM/ft²) | 132 | 72 | 83.5 | 110 |
| Open Area (%) | 1.85 | 1.48 | 1.53 | 1.12 |
| Average Pore Size, ECD (mils) | 3.47 | 2.69 | 4.08 | 3.64 |
| ECD COV (%) | 59.6 | 66.2 | 64.2 | 63.8 |

TABLE 3

| | Example 9 | Example 10 | Example 11 | Example 12 |
|---|---|---|---|---|
| Precursor Film | | | | |
| Film Designations | XLP-980 | XLP-980 | XLP-980 | XLP-980 |
| Film Type | Blend | Blend | Blend | Blend |
| Film Composition | | | | |
| Polymer 1 | EXACT™ 3028 | EXACT™ 3028 | EXACT™ 3028 | EXACT™ 3028 |
| Polymer 2 | LDPE | LDPE | LDPE | LDPE |
| Ratio (Polymer 1: Polymer 2) | 80:20 | 80:20 | 80:20 | 80:20 |
| Thickness (mils) | 2.5 | 2.5 | 2.5 | 2.5 |
| MD Tensile Strength (at break) (lb/in) | 16.2 | 16.8 | 16.2 | 16.2 |
| CD Tensile Strength (at break) (lb/in) | 15.1 | 16.4 | 15.1 | 15.1 |
| MD Elongation (at break) (%) | 664 | 670 | 664 | 664 |
| CD Elongation (at break) (%) | 705 | 715 | 705 | 705 |
| Polymer 1 Properties | | | | |
| Density of Polymer 1 | 0.901 | 0.901 | 0.901 | 0.901 |
| Molecular Weight Distribution of Polymer 1 | 1.86 | 1.86 | 1.86 | 1.86 |
| Melt Index (g/10 min) of Polymer 1 | 1.17 | 1.17 | 1.17 | 1.17 |
| Web Fabrication Conditions | | | | |
| Forming surface | B | C | F | G |
| Orifice Diameter (mils) | 5 | 5 | 5 | 5 |
| Number of orifices per inch | 50 | 50 | 50 | 50 |
| Number of manifolds | 3 | 3 | 3 | 3 |
| Water Temperature (°F.) | 162 | 165 | 160 | 160 |
| Manifold pressure (psi) | 1050 | 1450 | 1050 | 1250 |
| Line Speed (ft/min) | 72 | 165 | 72 | 72 |
| Web Properties | | | | |
| MD Tensile Strength (at break) (%) | 3.96 | 4.13 | 3.66 | 3.98 |
| CD Tensile Strength (at break) (%) | 3.14 | 3.31 | 2.89 | 3.32 |
| % Recovery after 50% CD stretch | 78.7 | 77.1 | 72.3 | 77.8 |
| Stretch Force at 50% stretch (lb/in) | 1.18 | 0.88 | 0.79 | 0.76 |
| Recovery Energy/Stretch Energy at 50% stretch (× 100) | 49.9 | 53.0 | 48.2 | 51.8 |
| MVTR after adhesive coating (g/m²/24 hrs) | 2300 | 4400 | 3900 | 3100 |
| Frazier Air Permeability (CFM/ft²) | 97.5 | 141 | 133 | 55 |
| Open Area (%) | 1.62 | 2.09 | 2.42 | 0.72 |
| Average Pore Size, ECD (mils) | 3.62 | 4.12 | 4.49 | 2.75 |
| ECD COV (%) | 73.2 | 61.7 | 71.1 | 78.9 |

Figure 8A:
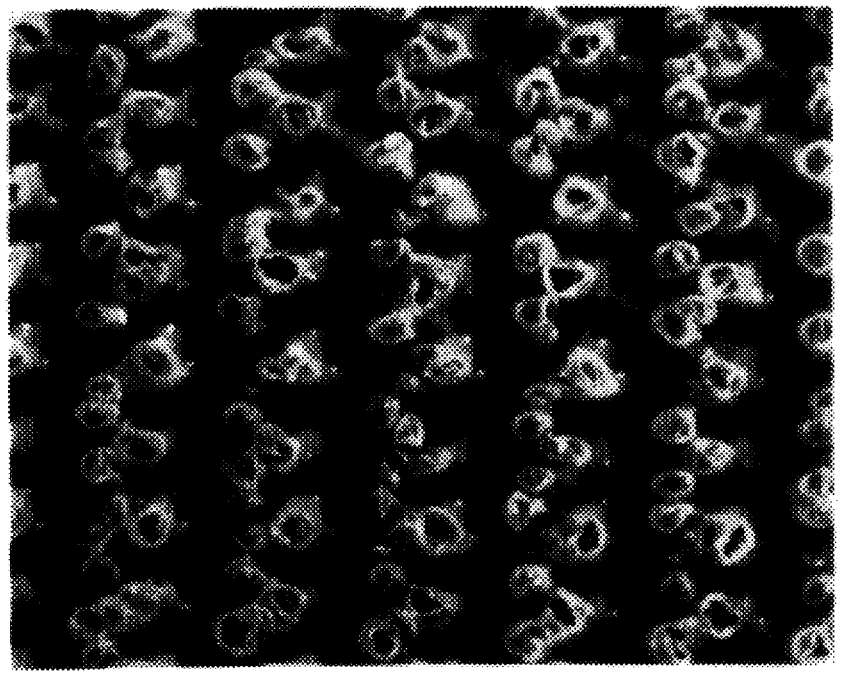
FIGS. 8A, 8B, 9A, 9B, 10A, 10B, 11A, 11B, 12A, and 12B are photographs of plan views of apertured web specimens enlarged 15 times actual size.
Figure 8B:
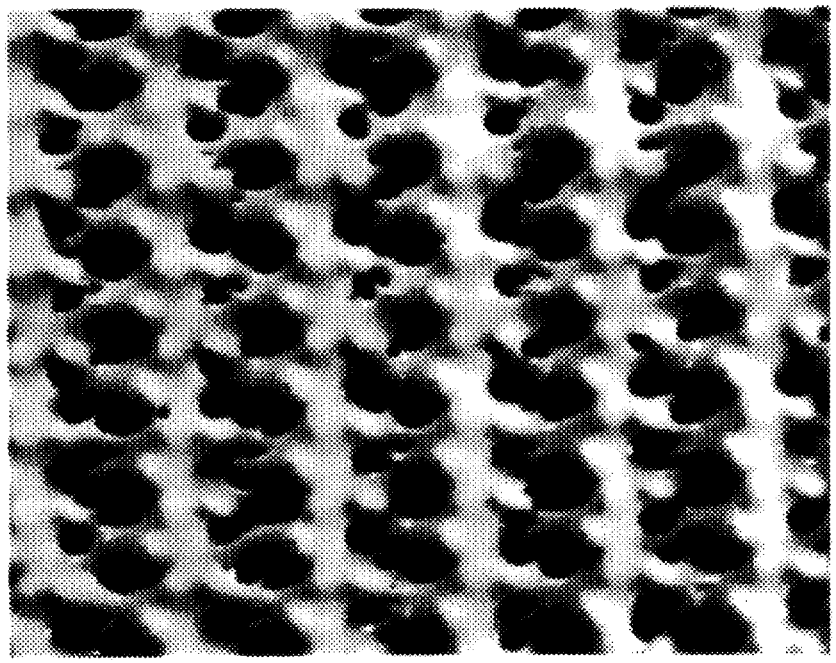
Figure 9A:
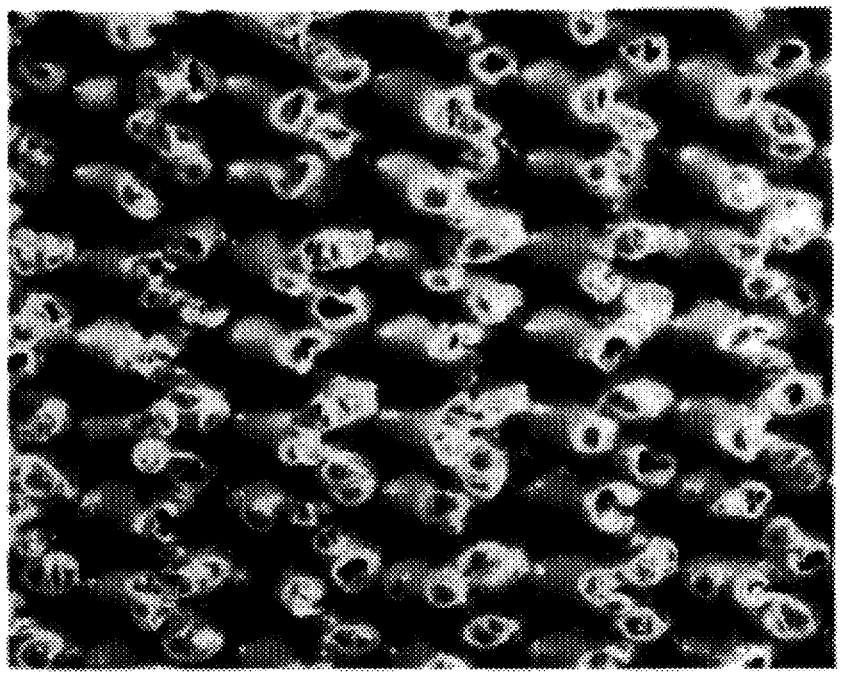
Figure 9B:
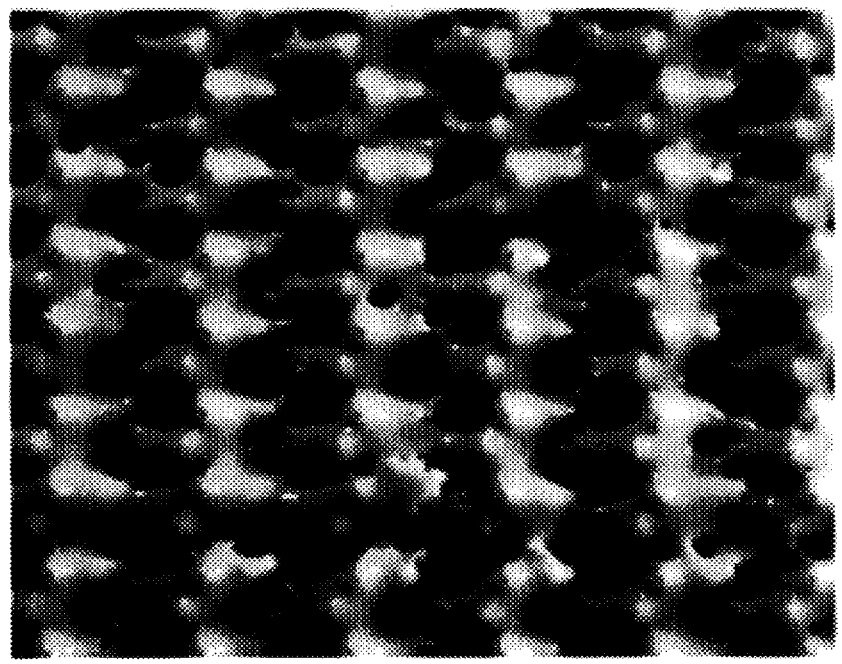
Figure 10A:
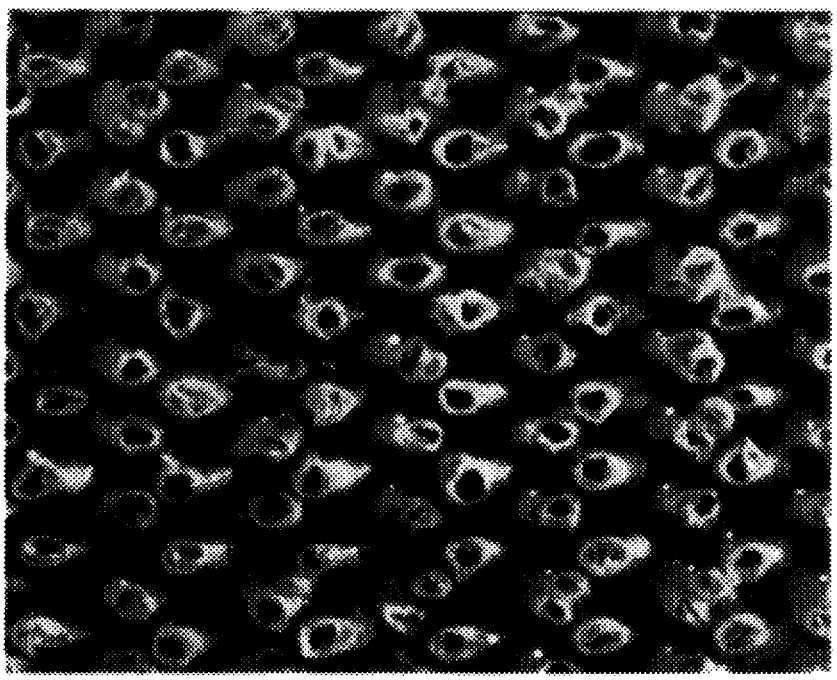
Figure 10B:
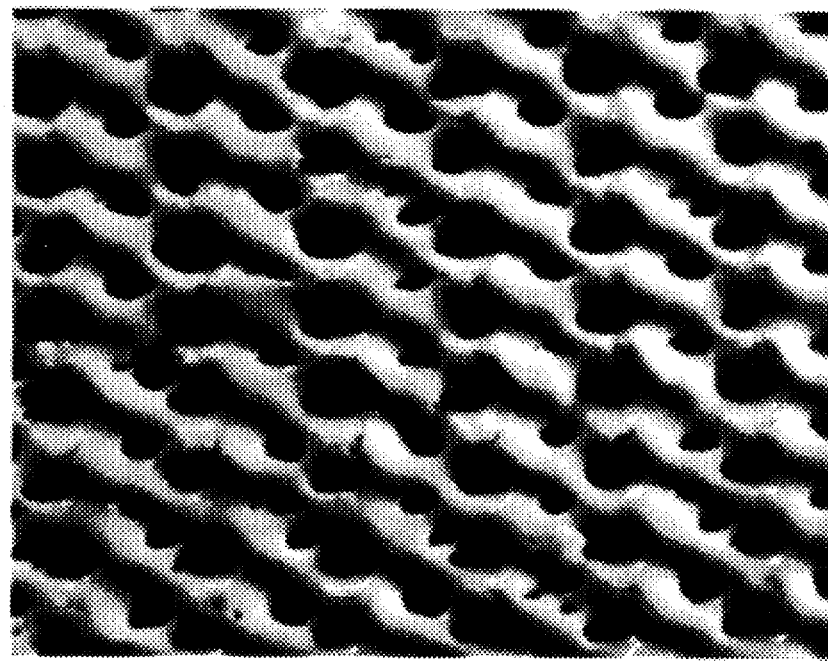
Figure 11A:
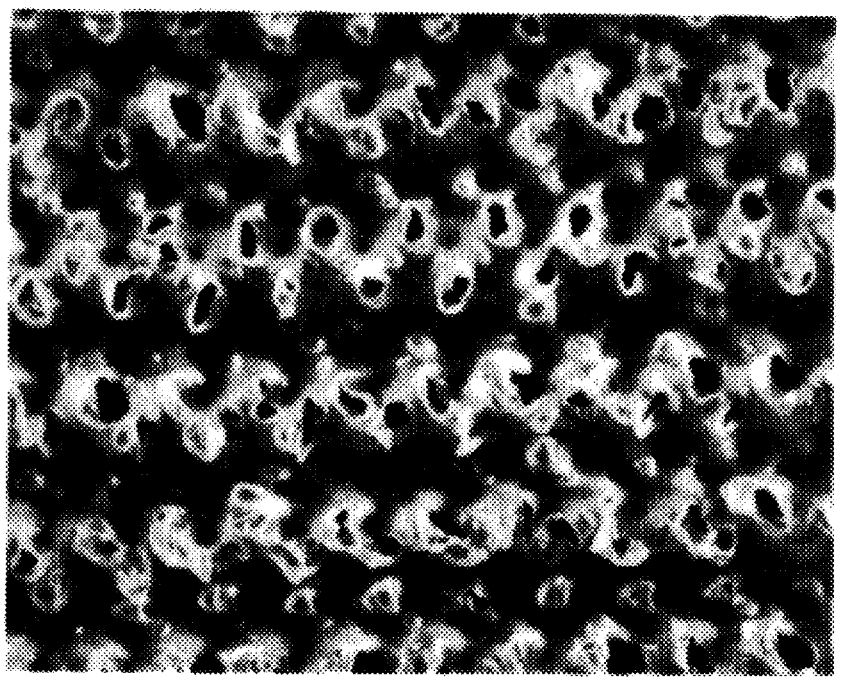
Figure 11B:
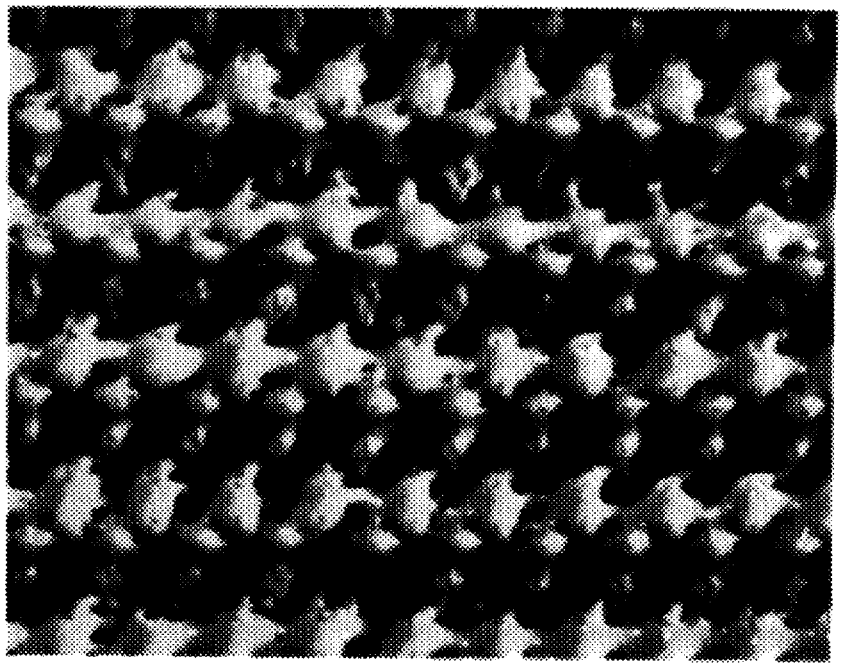
Figure 12A:
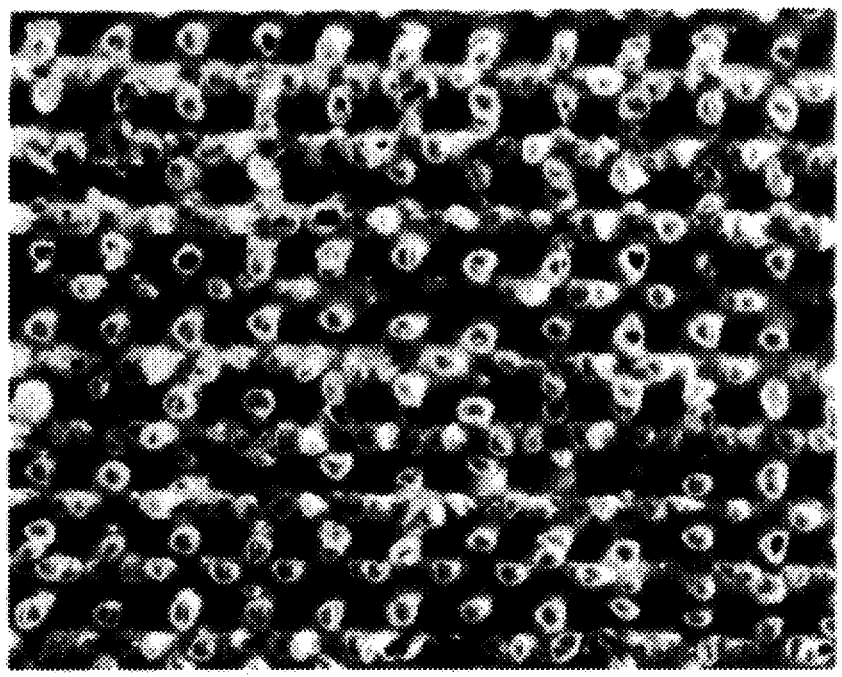
Figure 12B:
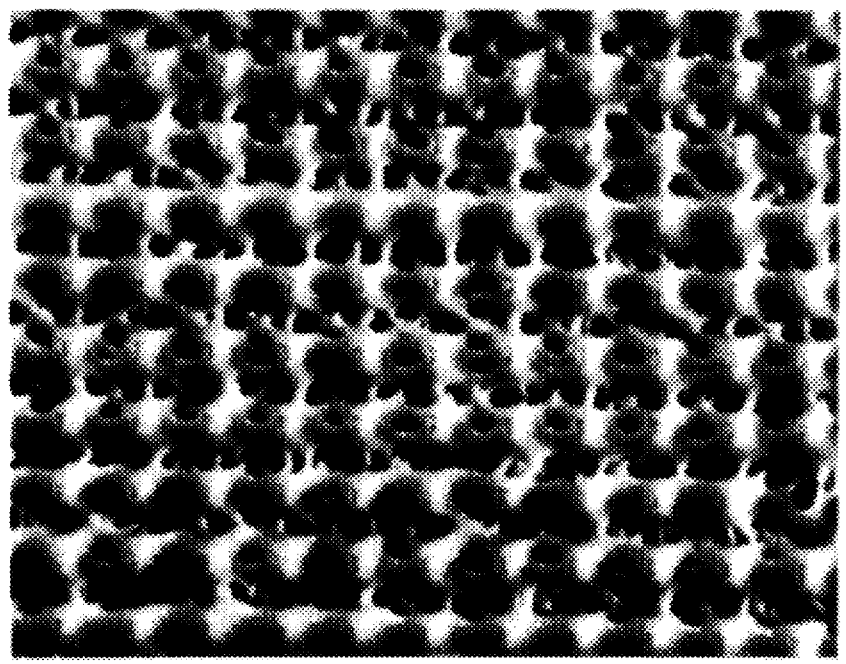

FIGS. 8A and 8B, 9A and 9B, 10A and 10B, 11A and 11B, and 12A and 12B are photographs of plan views of the film or web samples enlarged many times actual size. In particular, the Figures with the "A" suffix show the side of the film facing the forming surface or sleeve, and the "B" suffix Figures show the film surface facing away from the forming surface (i.e., facing toward the water jets). The web or film of Example 8 is shown in FIGS. 8A and 8B, the film of Example 9 is shown in FIGS. 9A and 9B, the film of Example 10 is shown in FIGS. 10A and 10B, the film of Example 11 is shown in FIGS. 11A and 11B, and the film of Example 12 is shown in FIGS. 12A and 12B.

Figure 13:
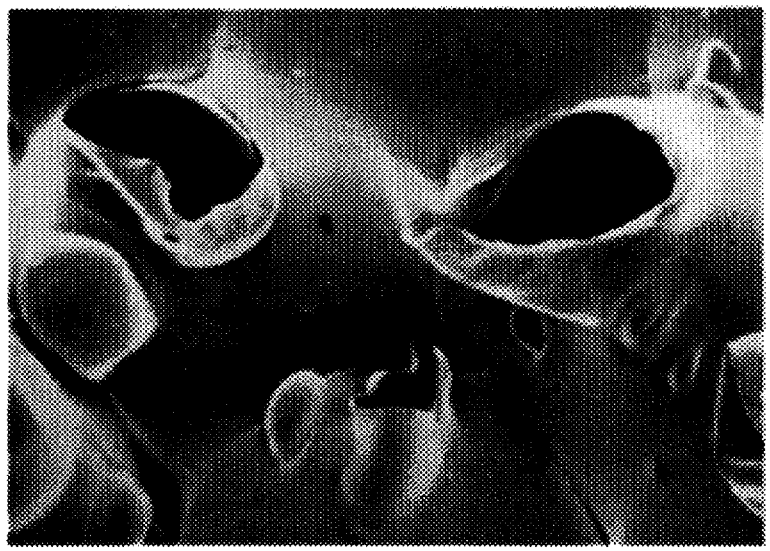
FIG. 13 is a photograph of a web specimen enlarged 100 times.

FIG. 13 is an even more greatly enlarged photograph of a film sample taken from the film side that faced the forming surface or sleeve, and the apertured film was formed from a precursor film XLP-980 (the properties of which film XLP-980 are listed in Example 4 of Table 1).

Figure 4:
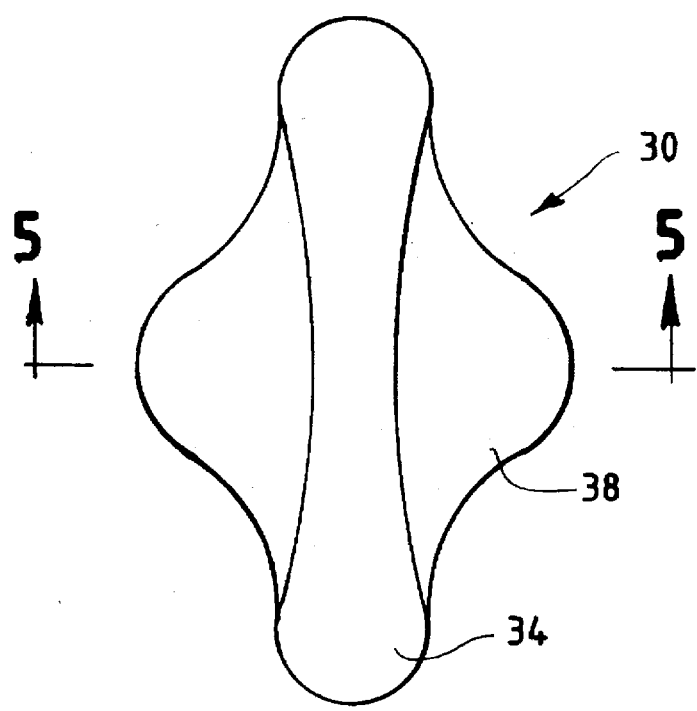
FIG. 4 is a simplified, perspective representation of a sanitary pad incorporating the web of the present invention.
Figure 5:
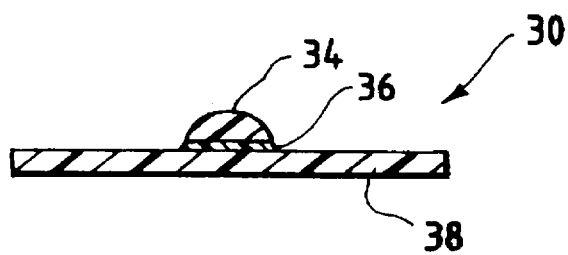
FIG. 5 is an enlarged, fragmentary cross-sectional view taken generally along the plane 5—5 of FIG. 4, the components' thicknesses having been greatly exaggerated for ease of illustration.

A second embodiment of the present invention is incorporated in a sanitary pad 30 illustrated in FIGS. 4 and 5. The pad 30 includes an absorbent panel 34 secured to a backing web 38 with a layer or lines of adhesive 36. The absorbent panel 34 may be of any suitable special design or conventional design well known to those of skill in the art.

The backing web 38 is an apertured web in accordance with the teachings of the present invention and includes a suitably shaped, apertured film having the structure and composition that is identical with the structure and composition of the film employed in the backing web 20 described above in detail with respect to the bandage 10 illustrated in FIGS. 1, 2, and 3. The sanitary pad 30 may include other conventional features (not illustrated) well known to those of skill in the art.

Figure 6:
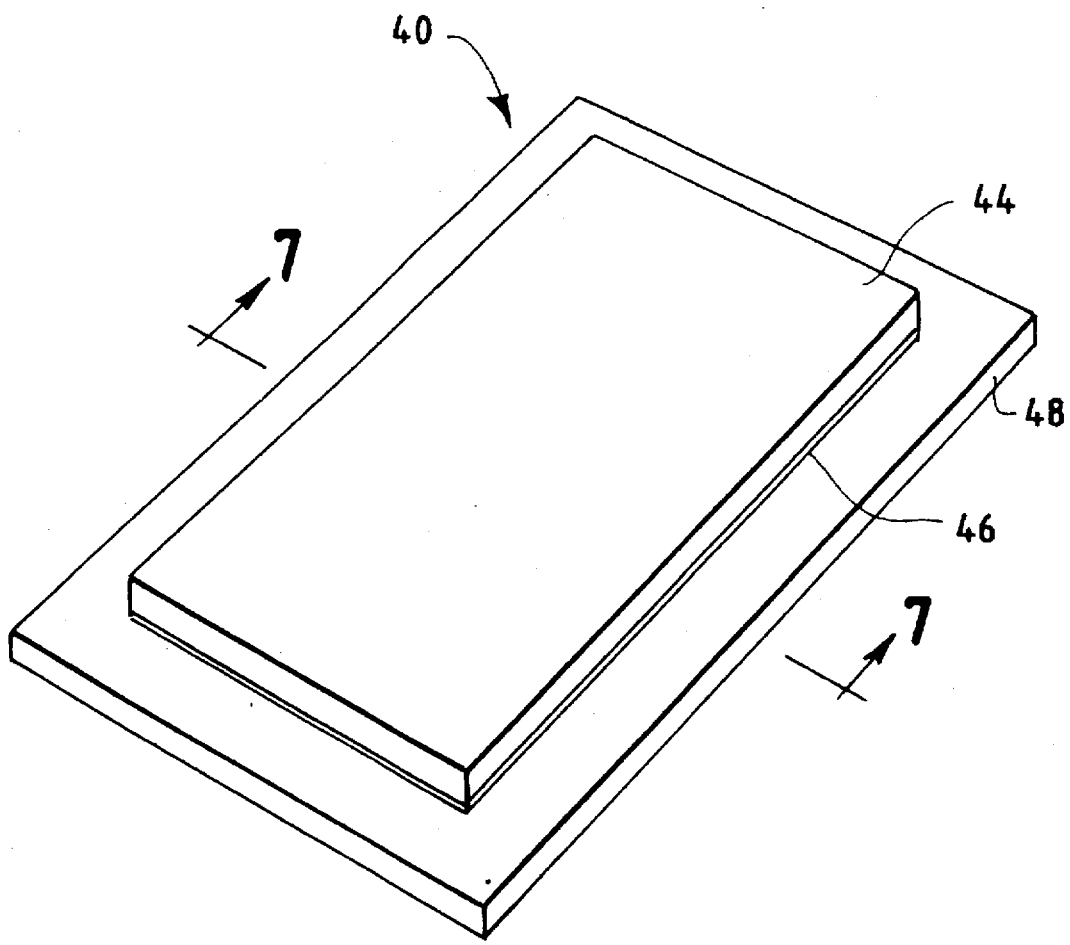
FIG. 6 is a simplified perspective representation of an unfolded disposable diaper incorporating the web of the present invention, the components' thicknesses having been greatly exaggerated for ease of illustration.
Figure 7:
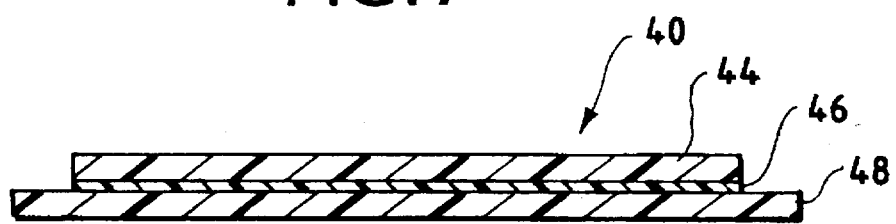
FIG. 7 is an enlarged, fragmentary cross-sectional view taken generally along the plane 7—7 in FIG. 6.

A third embodiment of the present invention is incorporated in a disposable diaper 40 illustrated in 5 FIGS. 6 and 7. The diaper 40 includes an absorbent panel 44 secured to a backing web 48 with a layer or strips of adhesive 46. The absorbent panel 44 may be of any suitable special design or any conventional design well known to those of skill in the art. The backing web 48 is an apertured web in accordance with the teachings of the present invention and includes a suitably shaped, apertured film having the structure and composition identical with the structure and composition of the film employed in the backing web 20 described above in detail with respect to the bandage 10 illustrated in FIGS. 1, 2, and 3. The diaper 40 may include other conventional features (not illustrated) well known to those of skill in the art.

When the backing sheet or web is fabricated and incorporated in an article in accordance with the invention as described above, the article web provides highly desirable characteristics. Owing to the high flexibility and elasticity of the web, the article can more easily conform to the part of the body with which it is in contact and can more easily accommodate significant stretching with relatively low forces and with high recovery. While the web resists water and can be made relatively impervious or non-absorbent to liquids, it is breathable so as to permit the transfer of water vapor from the skin to the ambient air. The web readily accepts adhesive coating and is radiation sterilizable. The web is relatively tough and can withstand externally applied forces well enough to avoid damage from abrasion or snagging during normal use of the article. The web accepts coloring, printing, and surface patterns. Importantly, the web has the soft feel and drape of cloth. Further, the web has good processability characteristics and can be produced by methods that minimize manufacturing costs.

It will be readily apparent from the foregoing detailed description of the invention and from the illustrations thereof that numerous variations and modifications may be effected without departing from the true spirit and scope of the novel concepts or principles of this invention.

What is claimed:

1. A web suitable for contact with skin, said web comprising a polymeric film having apertures providing breathability with resistance to water permeation and absorption and providing flexibility with an elasticity accommodating a stretch elongation of at least 50% and a recovery of at least 65% from a stretch elongation of 50%.

2. The web in accordance with claim 1 in which said web is secured to an absorbent panel;

said web includes an adhesive coating on the side facing said absorbent panel; and said web is in combination with at least an absorbent panel to define one of the following: a bandage, a disposable diaper, a feminine sanitary protection article, and an adult incontinent device adapted to absorb exudate from an incontinent person.

3. The web in accordance with claim 1 in which said apertured film is produced from a solid precursor film comprising a copolymer of ethylene and a comonomer polymerized using a single-site metallocene-type polymerization catalyst;

said comonomer comprises styrene, ethylenically unsaturated olefin(s) having from 3 to about 20 carbon atoms, or combinations thereof;

said precursor film includes additional constituents, including low density polyethylene;

said web includes a first side having a three-dimensional surface structure and includes an oppositely facing second side having a three-dimensional surface structure;

said first side has first, second, third, and fourth surfaces, said first surface defining a plurality of wales, said second surface sloping to connect said first surface and said third surface, said third surface having macroscopic apertures arranged generally in rows; and said fourth surface having holes and bubbles; and said second side exhibits generally a negative image of said first side and includes clusters of tubes terminating in holes and deflated balloon-like bubbles imparting a fabric-like feel to said web.

4. The web in accordance with claim 1 in which said web elasticity is such that a tension force within a range of 0.5 to 2.5 pounds per inch of film will produce a 50% stretch elongation with a recovery of at least 70%;

said web is produced from a solid precursor film;

said precursor film comprises a polymer with
a density in the range of about 0.86 to about 0.93 g/cm$^3$,
a molecular weight distribution in the range of about 1.0 to about 3.50, and
a melt index in the range of about 1.0 to about 3.0 g/10 min;

said web is produced from said precursor film by subjecting said precursor film to forming forces sufficient to form permanent localized deformations therein and create apertures therein;

said web has a film thickness in the range of about 2.25 to about 30 mils, has a basis weight in the range of about 0.7 to about 4.7 oz/yd$^2$, and exhibits a ratio of recovery energy to stretch energy multiplied by 100 that is greater than 25 for a 50% stretch elongation;

said web has a tensile strength at break in a range of about 2 to about 7 pounds per inch of web;

said web has an elongation at break in a range of about 200 to about 500 percent as said web is elongated in any direction;

said web has a Frazier air permeability in the range of about 20 to about 300 cubic feet per minute per square foot;

said apertures are irregularly shaped;

said web has an average hole size expressed as an equivalent circular diameter (ECD) in the range of about 1.0 to about 10 mils;

said web has an open area in the range of about 0.5 to about 20 percent;

said web has an ECD COV in the range of about 18 to about 79 percent; and said web has a moisture vapor transfer rate greater than about 300 g/m$^2$/24 hrs.

5. A disposable absorbent article comprising:

an absorbent panel; and a backing web secured to said absorbent panel, said web comprising an apertured film produced from a solid precursor film comprising a copolymer of ethylene and a comonomer polymerized using a single-site metallocene-type polymerization catalyst, said film having localized deformations and apertures therein, said film exhibiting breathability, strength, and flexibility with an elasticity accommodating stretch elongation and at least partial recovery wherein said elasticity accommodates a stretch elongation of at least 50% and a recovery of at least 65% from a stretch elongation of 50%.

6. The article in accordance with claim 5 in which said apertured film has a thickness in the range of about 2.25 to about 30 mils, has a basis weight in the range of about 0.7 to about 4.5 oz/yd$^2$, and exhibits (1) an elasticity accommodating at least a 50% stretch elongation when subjected to a tension force in a range of about 0.5 to about 2 pounds per inch of film, (2) a recovery of at least 70% from a 50% stretch elongation, and (3) a ratio of recovery energy to stretch energy multiplied by 100 that is greater than 25 for a 50% stretch elongation;

said apertured film has a tensile strength at break in a range of about 2 to about 7 pounds per inch of film;

said apertured film has an elongation at break in a range of about 200 to about 500 percent as said film is elongated in any direction;

said apertured film has a Frazier air permeability in the range of about 20 to about 300 cubic feet per minute per square foot;

said apertures are irregularly shaped;

said apertured film has an average hole size expressed as an equivalent circular diameter (ECD) in the range of about 1.0 to about 10 mils;

said apertured film has an open area in the range of about 0.5 to about 20 percent;

said apertured film has an ECD COV in the range of about 18 to about 79 percent; and said apertured film has a moisture vapor transfer rate greater than about 300 g/m$^2$/24 hrs.

7. The article in accordance with claim 5 in which said web includes an adhesive coating on the side facing said absorbent panel; and said article is one of the following: a wound dressing, a disposable diaper, a feminine sanitary protection article, and an adult incontinent device adapted to absorb exudate from an incontinent person.

8. The article in accordance with claim 5 in which said apertured film includes a first side having a three-dimensional surface structure and includes an oppositely facing second side having a three-dimensional surface structure;

said first side has first, second, third, and fourth surfaces, said first surface defining a plurality of wales, said second surface sloping to connect said first surface and said third surface, said third surface having macroscopic apertures arranged generally in rows; and said fourth surface having holes and bubbles; and said second side exhibits generally a negative image of said first side and includes clusters of tubes terminating in holes and deflated balloon-like bubbles imparting a fabric-like feel to said apertured film.

9. A disposable absorbent article comprising:

an absorbent panel; and a backing web secured to said absorbent panel, said web comprising an apertured film produced from a solid polymeric precursor film wherein said apertured film has apertures and exhibits an elasticity such that a tension force within the range of about 0.5 to about 2.5 pounds per inch of film will produce a 50% stretch elongation with a recovery of at least 65%.

10. The article in accordance with claim 9 in which said article is one of the following: a wound dressing, a disposable diaper or an adult incontinent device adapted to absorb exudate from an incontinent person, and a feminine sanitary protection article.

11. The article in accordance with claim 9 in which said web includes an adhesive coating on the side facing said absorbent panel;

said apertured film is produced from a solid precursor film comprising a copolymer of ethylene and a comonomer polymerized using a single-site metallocene-type polymerization catalyst;

said apertured film includes a first side having a three-dimensional surface structure and includes an oppositely facing second side having a three-dimensional surface structure;

said first side has first, second, third, and fourth surfaces, said first surface defining a plurality of wales, said second surface sloping to connect said first surface and said third surface, said third surface having macroscopic apertures arranged generally in rows; and said fourth surface having holes and bubbles; and said second side exhibits generally a negative image of said first side and includes clusters of tubes terminating in holes and deflated balloon-like bubbles imparting a fabric-like feel to said apertured film.

12. The article in accordance with claim 9 in which said apertured film has a thickness in the range of about 2.25 to about 30 mils, has a basis weight in the range of about 0.7 to about 4.5 oz/yd$^2$, and exhibits (1) an elasticity accommodating at least a 50% stretch elongation when subjected to a tension force in a range of about 0.5 to about 2 pounds per inch of film, (2) at least 70% recovery from a 50% stretch elongation, and (3) a ratio of recovery energy to stretch energy multiplied by 100 that is greater than 25 for a 50% stretch elongation;

said apertured film has a tensile strength at break in a range of about 2 to about 7 pounds per inch of film;

said apertured film has an elongation at break in a range of about 200 to about 500 percent as said film is alongated in any direction ;

said apertured film has a Frazier air permeability in the range of about 20 to about 300 cubic feet per minute per square foot;

said apertures are irregularly shaped;

said apertures have an average hole size expressed as an eequivalent diameter (ECD) in the range of about 1.0 to about 10 mils;

said apertured film has an open area in the range of about 0.5 to about 20 percent;

said apertured film has ECD COV in the range of about 18 to about 79 percent; and said apertured film has a moisture vapor transfer rate greater than about 300 g/m$^2$/24 hrs.

13. A disposable absorbent article comprising:

an absorbent panel; and a backing web secured to said absorbent panel, said web comprising a polymeric film having apertures, said film exhibiting an elasticity accommodating at least a 50% stretch elongation when subjected to a tension force of at least 0.5 pounds per inch of film and exhibiting a recovery of at least 65% from a stretch elongation of 50%.

14. The article in accordance with claim 13 in which said article is one of the following:

a wound dressing;

a disposable diaper or an adult incontinent device adapted to absorb exudate from an incontinent person; or a feminine sanitary protection article.

15. The article in accordance with claim 13 in which
said web includes an adhesive coating on the side facing said absorbent panel;
said apertured film is produced from a solid precursor film comprising a copolymer of ethylene and a comonomer polymerized using a single-site metallocene-type polymerization catalyst;
said apertured film includes a first side having a three-dimensional surface structure and includes an oppositely facing second side having a three-dimensional surface structure;
said first side has first, second, third, and fourth surfaces, said first surface defining a plurality of wales, said second surface sloping to connect said first surface and said third surface, said third surface having macroscopic apertures arranged generally in rows; and said fourth surface having holes and bubbles; and
said second side exhibits generally a negative image of said first side and includes clusters of tubes terminating in holes and deflated balloon-like bubbles imparting a fabric-like feel to said apertured film.

16. The article in accordance with claim 13 in which
said film has a thickness in the range of about 2.25 to about 30 mils, has a basis weight in the range of about 0.7 to about 4.5 oz/yd$^2$, and exhibits (1) an elasticity accommodating at least a 50% stretch elongation when subjected to a tension force in a range of about 0.5 to about 2 pounds per inch of film, (2) at least 70% recovery from a 50% stretch elongation, and (3) a ratio of recovery energy to stretch energy multiplied by 100 that is greater than 25 for a 50% stretch elongation;
said apertured film has a tensile strength at break in a range of about 2 to about 7 pounds per inch of film;
said apertured film has an elongation at break in a range of about 200 to about 500 percent as said film is elongated in any direction;
said apertured film has a Frazier air permeability in the range of about 20 to about 300 cubic feet per minute per square foot;
said apertures are irregularly shaped;
said apertures have an average hole size expressed as an equivalent circular diameter (ECD) in the range of about 1.0 to about 10.0 mils;
said apertured film has an open area in the range of about 0.5 to about 20 percent;
said apertured film has an ECD COV in the range of about 18 to about 79 percent; and
said apertured film has a moisture vapor transfer rate greater than about 300 g/m$^2$/24 hrs.

17. A disposable absorbent article comprising:
an absorbent panel; and
a backing web secured to said absorbent panel, said web comprising an apertured film produced from a solid precursor film comprising a copolymer of ethylene and a comonomer polymerized in a structure using a single-site metallocene-type polymerization catalyst, said copolymer having
a density in the range of about 0.86 to about 0.93 g/cm$^3$,
a molecular weight distribution in the range of about 1.0 to about 3.50, and
a melt index in the range of about 0.5 to about 10.0 g/10 min.; and
said apertured film being produced from said precursor film by subjecting said precursor film to forming forces sufficient to form permanent localized deformations therein and to create apertures therein.

18. The article in accordance with claim 17 in which
said web includes an adhesive coating on the side facing said absorbent panel; and
said article is one of the following: a wound dressing, a disposable diaper, a feminine sanitary protection article, and an adult incontinent device adapted to absorb exudate from an incontinent person.

19. The article in accordance with claim 17 in which
said apertured film includes a first side having a three-dimensional surface structure and includes an oppositely facing second side having a three-dimensional surface structure;
said first side has first, second, third, and fourth surfaces, said first surface defining a plurality of wales, said second surface sloping to connect said first surface and said third surface, said third surface having macroscopic apertures arranged generally in rows; and said fourth surface having holes and bubbles; and
said second side exhibits generally a negative image of said first side and includes clusters of tubes terminating in holes and deflated balloon-like bubbles imparting a fabric-like feel to said apertured film.

20. The article in accordance with claim 17 in which
said apertured film has a thickness in the range of about 2.25 to about 30 mils, has a basis weight in the range of about 0.7 to about 4.50 oz/yd$^2$, and exhibits (1) an elasticity accommodating at least a 50% stretch elongation when subjected to a tension force in a range of about 0.5 to about 2 pounds per inch of film, (2) at least 70% recovery from a 50% stretch elongation, and (3) a ratio of recovery energy to stretch energy multiplied by 100 that is greater than 40 for a 50% stretch elongation;
said apertured film has a tensile strength at break in a range of about 2 to about 7 pounds per inch of film;
said apertured film has an elongation at break in a range of about 200 to about 500 percent as said film is elongated in any direction;
said apertured film has a Frazier air permeability in the range of about 20 to about 300 cubic feet per minute per square foot;
said apertures are irregularly shaped;
said apertures have an average hole size expressed as an equivalent circular diameter (ECD) in the range of about 1.0 to about 10 mils;
said apertured film has an open area in the range of about 0.5 to about 20 percent;
said apertured film has an ECD COV in the range of about 18 to about 79 percent; and
said apertured film has a mass vapor transfer rate greater than about 300 g/m$^2$/24 hrs.

* * * * *

UNITED STATES PATENT AND TRADEMARK OFFICE
CERTIFICATE OF CORRECTION

PATENT NO. : 5,681,301

DATED : October 28, 1997

INVENTOR(S) : Ching-Yun Morris Yang; Mordechai Turi, and William Chien-Chung Hsu It is certified that error appears in the above-indentified patent and that said Letters Patent is hereby corrected as shown below:

Column 5, line 55, the formula should read:

$$immediate\ recovery = \frac{(Le-Lt)}{(Le-Lo)} \times 100$$

Column 6, line 5, "a is" should be --and is--.

Column 6, line 64, before "test" delete "10".

Column 9, line 21, before "66" delete "10".

Column 10, line 12, after "removed" delete "5".

Column 15, line 29, before "and" insert --503--.

Column 15, line 37, before "and" (first occurrence) insert --511--.

Column 18, lines 20-30, the title of the third column of TABLE D should be changed to --Laser Bit Map Instructions-- and the title of the fourth column of TABLE D should be changed to --Smallest Repeat Element Of Laser Bit Map--.

Column 18, line 32, in the last line in the first column of TABLE D, "$^{11}F^2$" should be --$F^2$--.

UNITED STATES PATENT AND TRADEMARK OFFICE
CERTIFICATE OF CORRECTION

PATENT NO. : 5,681,301
DATED : October 28, 1997
INVENTOR(S) : Ching-Yun Morris Yang; Mordechai Turi, and William Chien-Chung Hsu It is certified that error appears in the above-indentified patent and that said Letters Patent is hereby corrected as shown below:

Column 19, line 44 in TABLE 1, "(%)" should be --(lb/in)--.

Column 19, line 47 in TABLE 1, "(%)" should be --(lb/in)--.

Column 19, in TABLE 1, between "break) (%)" in line 47 and "% Recovery)" in line 48, insert:

--MD Elongation
  (at Break) (%)                              357
  CD Elongation
  (at break) (%)      480      211      412      445--.

Column 20, lines 54-57 in TABLE 2, "MD Tensile Strength (at break) (%)" should be --MD Tensile Strength (at break) (lb/in)--.

Column 20, lines 57-59 in TABLE 2, "CD Tensile Strength (at break) (%)" should be --CD Tensile Strength (at break) (lb/in)--.

Column 21, line 54 in TABLE 3, after "Distribution" insert --(Mn/Mn)--.

Column 22, line 16 in TABLE 3, delete "(%)" and insert --(lb/in)--.

UNITED STATES PATENT AND TRADEMARK OFFICE
CERTIFICATE OF CORRECTION

PATENT NO. : 5,681,301
DATED : October 28, 1997
INVENTOR(S) : Ching-Yun Morris Yang; Mordechai Turi, and William Chien-Chung Hsu It is certified that error appears in the above-indentified patent and that said Letters Patent is hereby corrected as shown below:

Column 22, line 17 in TABLE 3, under Example 12, "3.32" should be --3.23--.

Column 22, line 19 in TABLE 3, "break) (%)" should be --break) (lb/in)--.

Column 22, after line 19 in TABLE 3, before "% Recovery" insert:

--MD Elongation
   (at break) (%)     480     460     390     490

CD Elongation
   (at break) (%)     385     360     240     390--.

Column 22, line 21 in TABLE 3, after "stretch" insert --(x100)--.

Column 23, line 4, delete "5".

Signed and Sealed this

Tenth Day of March, 1998

Attest:

BRUCE LEHMAN

*Attesting Officer*     *Commissioner of Patents and Trademarks*